United States Patent
Giliyar et al.

(10) Patent No.: US 10,709,716 B2
(45) Date of Patent: *Jul. 14, 2020

(54) 17-HYDROXYPROGESTERONE ESTER-CONTAINING ORAL COMPOSITIONS AND RELATED METHODS

(71) Applicant: Lipocine Inc., Salt Lake City, UT (US)

(72) Inventors: Chandrashekar Giliyar, Plymouth, MN (US); Srinivasan Venkateshwaran, Salt Lake City, UT (US); Basawaraj Chickmath, Minneapolis, MN (US); Satish Kumar Nachaegari, Holladay, UT (US); Nachiappan Chidambaram, Sandy, UT (US); Mahesh V. Patel, Salt Lake City, UT (US)

(73) Assignee: Lipocine Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/368,431

(22) Filed: Mar. 28, 2019

(65) Prior Publication Data

US 2019/0307775 A1    Oct. 10, 2019

Related U.S. Application Data

(63) Continuation of application No. 16/010,188, filed on Jun. 15, 2018, now abandoned, which is a
(Continued)

(51) Int. Cl.
*A61K 31/56* (2006.01)
*A61K 31/57* (2006.01)
(Continued)

(52) U.S. Cl.
CPC .............. *A61K 31/57* (2013.01); *A61K 8/63* (2013.01); *A61K 9/0053* (2013.01); *A61K 9/14* (2013.01);
(Continued)

(58) Field of Classification Search
CPC ...................................................... A61K 31/56
See application file for complete search history.

(56) References Cited

U.S. PATENT DOCUMENTS 3,164,520 A    1/1965    Raymond
3,541,209 A    11/1970   Neumann
(Continued)

FOREIGN PATENT DOCUMENTS

CA    2512989 A1    8/2004
CA    2789238 A1    9/2011
(Continued)

OTHER PUBLICATIONS

Migally; "Effect of Castor Oil and Benzyl Benzoate Used as a Vehicle for Antiandrogens on the Adrenal Cortex;" Archives of Andrology; (1979); pp. 365-369; vol. 2, No. 4; <doi: 10.3109/01485017908987338 >.
(Continued)

*Primary Examiner* — San Ming R Hui
(74) *Attorney, Agent, or Firm* — Thorpe North and Western, LLP; David W. Osborne

(57) ABSTRACT

The present invention provides for bioavailable oral dosage forms containing esters of 17-hydroxyprogesterone as well as related methods. The oral dosage forms can be formulated for pregnancy support and can include a therapeutically effective amount of an ester of 17-hydroxyprogesterone and a pharmaceutically acceptable carrier. In another embodiment, a pharmaceutically acceptable oral dosage form for pregnancy support is provided. The pharmaceutically acceptable oral dosage can include a therapeutically effective amount of an ester of 17-hydroxyprogesterone and a pharmaceutically acceptable carrier. The oral dosage form can, when measured using a USP Type-II dissolution apparatus in 900 mL of deionized water with 0.5 (w/v) of sodium lauryl sulfate at 50 RPM at 37° C., release at least 20 wt %
(Continued)

of the dose of the ester of 17-hydroxyprogesterone after 60 minutes, or in the alternative release at least 20 wt % more after 60 minutes than an equivalently dosed oral dosage form without the carrier.

12 Claims, 2 Drawing Sheets

Related U.S. Application Data continuation of application No. 15/090,800, filed on Apr. 5, 2016, now Pat. No. 10,022,384, which is a continuation of application No. 14/477,771, filed on Sep. 4, 2014, now Pat. No. 9,358,298, which is a continuation of application No. 13/193,571, filed on Jul. 28, 2011, now Pat. No. 8,951,996.

(51) Int. Cl.
| | |
|---|---|
| A61K 9/48 | (2006.01) |
| A61K 9/00 | (2006.01) |
| A61K 9/14 | (2006.01) |
| A61K 9/16 | (2006.01) |
| A61K 9/20 | (2006.01) |
| A61K 8/63 | (2006.01) |
| A61Q 11/00 | (2006.01) |
| A61K 47/10 | (2017.01) |
| A61K 47/12 | (2006.01) |
| A61K 47/14 | (2017.01) |
| A61K 47/20 | (2006.01) |
| A61K 47/22 | (2006.01) |
| A61K 47/26 | (2006.01) |
| A61K 47/32 | (2006.01) |
| A61K 47/44 | (2017.01) |

(52) U.S. Cl.
CPC .......... *A61K 9/145* (2013.01); *A61K 9/1617* (2013.01); *A61K 9/1623* (2013.01); *A61K 9/1635* (2013.01); *A61K 9/1641* (2013.01); *A61K 9/1652* (2013.01); *A61K 9/1676* (2013.01); *A61K 9/2013* (2013.01); *A61K 9/2018* (2013.01); *A61K 9/2031* (2013.01); *A61K 9/2054* (2013.01); *A61K 9/2059* (2013.01); *A61K 9/4841* (2013.01); *A61K 9/4858* (2013.01); *A61K 9/4866* (2013.01); *A61K 47/10* (2013.01); *A61K 47/12* (2013.01); *A61K 47/14* (2013.01); *A61K 47/20* (2013.01); *A61K 47/22* (2013.01); *A61K 47/26* (2013.01); *A61K 47/32* (2013.01); *A61K 47/44* (2013.01); *A61Q 11/00* (2013.01); *A61K 2800/10* (2013.01)

(56) References Cited

U.S. PATENT DOCUMENTS

| | | | |
|---|---|---|---|
| 4,147,783 A | 4/1979 | Van Der Vies |
| 4,196,188 A | 4/1980 | Besins |
| 4,230,702 A | 10/1980 | Eckert et al. |
| 4,439,432 A | 3/1984 | Peat |
| 5,057,319 A | 10/1991 | Gottwald et al. |
| 5,140,021 A | 8/1992 | Maxson |
| 5,314,882 A | 5/1994 | Pantic et al. |
| 5,543,150 A | 8/1996 | Bologna et al. |
| 5,620,705 A | 4/1997 | Dong et al. |
| 5,633,011 A | 5/1997 | Dong et al. |
| 5,645,856 A | 7/1997 | Lacy |
| 5,770,227 A | 6/1998 | Dong et al. |
| 5,948,766 A | 9/1999 | Milan et al. |
| 6,086,916 A | 7/2000 | Agnus |
| 6,096,338 A | 8/2000 | Lacy |
| 6,117,450 A | 9/2000 | Dittgen et al. |
| 6,294,192 B1 | 9/2001 | Patel |
| 6,500,814 B1 | 12/2002 | Hesch |
| 6,544,553 B1 | 4/2003 | Hisha et al. |
| 6,602,521 B1 | 8/2003 | Ting et al. |
| 6,656,929 B1 | 12/2003 | Agnus et al. |
| 6,866,865 B2 | 3/2005 | Hsia et al. |
| 6,923,988 B2 | 8/2005 | Patel et al. |
| 7,431,941 B2 | 10/2008 | Besins et al. |
| 7,473,687 B2 | 1/2009 | Hoffman et al. |
| 7,884,093 B2 | 2/2011 | Creasy et al. |
| 7,943,602 B2 | 5/2011 | Bunschoten et al. |
| 7,976,871 B2 | 7/2011 | Vaya et al. |
| 8,133,507 B2 | 3/2012 | Yum et al. |
| 8,241,664 B2 | 8/2012 | Dudley et al. |
| 8,951,996 B2 | 2/2015 | Giliyar et al. |
| 2002/0131988 A1 | 9/2002 | Foster et al. |
| 2003/0022875 A1 | 1/2003 | Wilson et al. |
| 2003/0077297 A1 | 4/2003 | Chen et al. |
| 2003/0236236 A1 | 12/2003 | Chen et al. |
| 2004/0052824 A1 | 3/2004 | Abou Charca-Vernet et al. |
| 2004/0131553 A1 | 7/2004 | Besse |
| 2004/0266025 A1 | 12/2004 | Hickok et al. |
| 2005/0020553 A1 | 1/2005 | Alt et al. |
| 2005/0181041 A1 | 8/2005 | Goldman |
| 2006/0009509 A1 | 1/2006 | Grubb et al. |
| 2006/0275360 A1 | 12/2006 | Ahmed et al. |
| 2008/0188829 A1 | 8/2008 | Creasy |
| 2009/0098200 A1 | 4/2009 | Temtsin Krayz et al. |
| 2009/0123534 A1 | 5/2009 | Besins et al. |
| 2009/0264395 A1 | 10/2009 | Creasy |
| 2011/0152840 A1 | 6/2011 | Lee et al. |
| 2011/0312927 A1 | 12/2011 | Nachaegari et al. |
| 2011/0312928 A1 | 12/2011 | Nachaegari et al. |
| 2012/0148675 A1 | 6/2012 | Chickmath et al. |
| 2013/0023505 A1 | 1/2013 | Garfield et al. |
| 2013/0029947 A1 | 1/2013 | Nachaegari et al. |
| 2014/0271882 A1 | 9/2014 | Giliyar |
| 2014/0377317 A1 | 12/2014 | Giliyar et al. |
| 2015/0165049 A1 | 6/2015 | Giliyar et al. |

FOREIGN PATENT DOCUMENTS

| | | |
|---|---|---|
| CN | 1398590 A | 2/2003 |
| CN | 1446540 A | 10/2003 |
| CN | 1509720 A | 7/2004 |
| CN | 1623550 A | 6/2005 |
| JP | 2004/155780 A | 6/2004 |
| JP | 2006-524238 | 10/2006 |
| WO | WO 90/08537 A1 | 8/1990 |
| WO | WO 93/12797 A1 | 7/1993 |
| WO | WO 95/05807 A1 | 3/1995 |
| WO | WO 00/59482 A1 | 10/2000 |
| WO | WO 2003/077923 A1 | 9/2003 |
| WO | WO 2004/080438 A1 | 9/2004 |
| WO | WO 2006/128057 A2 | 11/2006 |
| WO | WO 2009/070794 | 6/2009 |
| WO | WO 2010/117873 A2 | 10/2010 |
| WO | WO 2011/053666 | 5/2011 |

OTHER PUBLICATIONS

Leichtnam et al.; "Testosterone Hormone Replacement Therapy: State-of-the-Art and Emerging Technologies;" Pharmaceutical Research; (Jun. 2006); pp. 1117-1132; vol. 23, No. 6; <doi: 10.1007/s11095-006-0072-5 >.

Pfeil et al.; "Current and Future Testosterone Delivery Systems for Treatment of the Hypogonadal Male;" Journal of Expert Opinion on Drug Delivery; (Apr. 21, 2008); pp. 471-481; vol. 5, Issue 4; <doi: 10.1517/17425247.5.4.471 >.

Supplementary Search Report dated Jul. 16, 2019, in EP Application No. 14764607.9, filed Jul. 27, 2012; 3 pages.

Saxton et al.; "Functional Effects of 17 Alpha-hydroxyprogesterone Caproate (17P) on Human Myometrial Contractility in Vitro." Reproductive Biology and Endocrinology; BMC; Dec. 7, 2004; vol. 2, Issue 80; 6 Pages.

(56) References Cited

OTHER PUBLICATIONS

De Lignieres; Oral Micronized Progesterone; Clinical Therapeutics; Jan. 1999; pp. 41-60; vol. 21, No. 1; Elsevier.
Defranco et al; Vaginal Progesterone is Associated with a Decrease in Risk for Early Preterm Birth and Improved Neonatal Outcome in Women with a Short Cervix: a Secondary Analysis from a Randonnzed, Double-Blind; Placebo-Controlled Trial; Ultrasound in Obsetrics and Gynecology; Oct. 2007; pp. 697-705; vol. 30, No. 5; John Wiley & Sons, Inc.
Emerald Performance Materials; Benzyl Benzoate; Product Information Bulletin; upon belief and knowledge prior to May 17, 2013; 3 pages; Revision 01; Emerald Kalama Chemical, LLC.
Facchinetti et al, Am. J. Obstet. Gynecol., 2007, 196(453), e1-4 discussion 421.
FDA; 17a Alpha Hydroxyprogesterone Caproate for Prevention of Preterm Birth, Overview of FDA Background Document; Aug. 2, 2006; 62 pages (see introduction); Food and Drug Administration.
Greene; Progesterone and Preterm Delivery—Déjà. Vu All Over Again; The New England Journal of Medicine; Jun. 12, 2003; pp. 2453-2455; vol. 348, No. 24; Massachusetts Medical Society.
Johnson et al, N. Engl. J. Med., 1975, 293, p. 675-680.
Levy et al.; Pharmacokinetics of Natural Progesterone Administered in the Form of a Vaginal Tablet; Human Reproduction; Mar. 1999; pp. 606-610; vol. 14, No. 3; European Society of Human Reproduction and Embryology.
Mets et al, N. Engl. J. Med., 2003, 348, p. 2379-2385.
O'Brien et al; Progesterone Vaginal Gel for the Reduction of Recurrent Preterm Birth: Primary Results From a Randomized, Double-Blind, Placebo-Controlled Trial; Ultrasound in Obstetrics and Gynecology; Oct. 2007; pp. 687-696; vol. 30, No. 5; John Wiley & Sons, Inc.
Rai et al.; Oral Micronized Progesterone for Prevention of Preterm Birth; International Journal of Gynecology and Obstetrics; Jan. 2009, pp. 40-43; vol. 104, No. 1; Elsevier.
Rogers et al.; Micronized powders of a poorly water soluble drug produced by a spray-freezing into liquid-emulsion process; European Journal of Pharmaceutics and Biopharmaceutics; Mar. 2003; pp. 161-172; vol. 55; Elsevier.
Sexton et al; Functional effects of 17 alpha-hydroxyprogesterone caproate (17P) on human myometrial condtractility in vitro; Reproductive Biology and Endocrinology; Dec. 7, 2004; 6 pages; vol. 2, No. 80; Biomed Central.
Alan Thevenet N. Tita et al., American Journal of Obstetrics and Gynecology; Mar. 2009:219-224.
Vidaeff et al.; Critical appraisal of the efficacy, safety, and patient acceptability of hydroxyprogesterone caproate injection to reduce the risk of preterm birth; Patent Preference and Adherence; Jul. 11, 2013; pp. 683-691; Dove Medical Press Ltd.
Wikipedia; 17-Hydroxyprogesterone; Wikipedia, The Free Encyclopedia; http://en.wikipedia.org/wiki/17-Hydroxyprogesterone; as accessed Apr. 22, 2011; 5 pages; Wikimedia Foundation, Inc.
Aufrere et al.; Progesterone: An Overview and recent Advances; Journal of Pharmaceutical Sciences; Jun. 1976; pp. 783-800; vol. 65, No. 6; Elsevier.
Merck Manual; Oral Contraception; Merck Manual; 1995; pp. 1701-1706; $16^{th}$ Ed., Third Printing.
Nihon Sankafujinka Gakkaihen; Teiyouryou Keikou Hininyaku no Shiyuou in kan suru Gaidorain; 2005; 69 pages.
Hargrove et al.; "Absorption of oral progesterone is influenced by vehicle and particle size"; American Journal of Obstetrics and Gynecology; (Oct. 1989); pp. 948-951; vol. 161, Issue 4; <doi: 10.1016/0002-9378(89)90759-X > [abstract].
Ratner et al.; "Menopause and hormone-replacement therapy; Part 2: Hormone-replacement therapy regimens"; West Journal of Medicine; (Jul. 2001); pp. 32-34; vol. 175, No. 1.

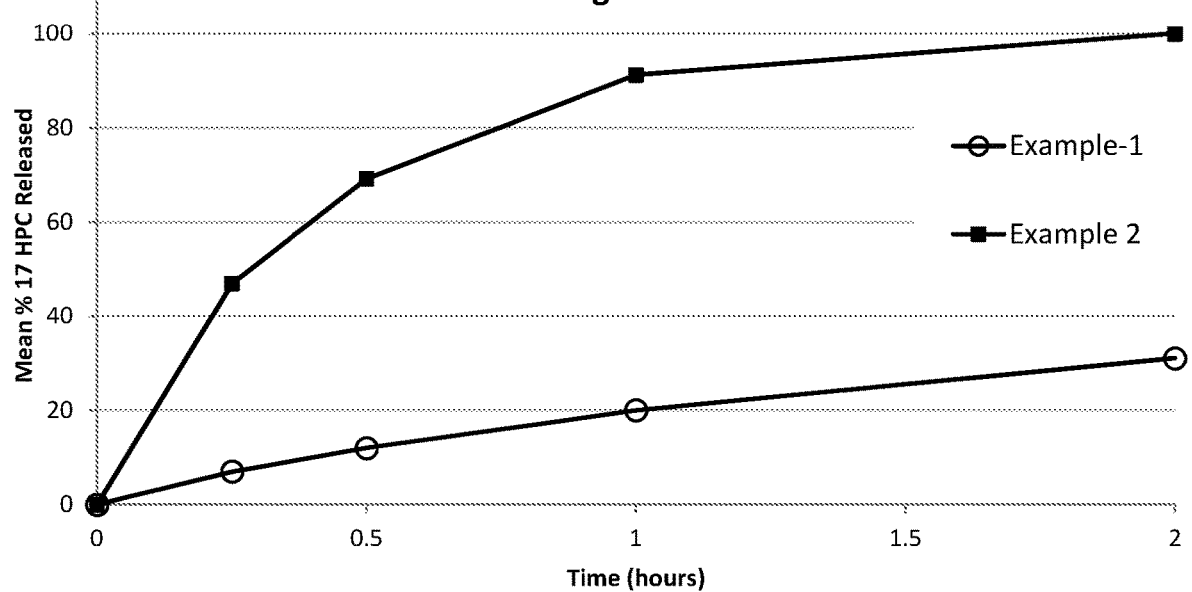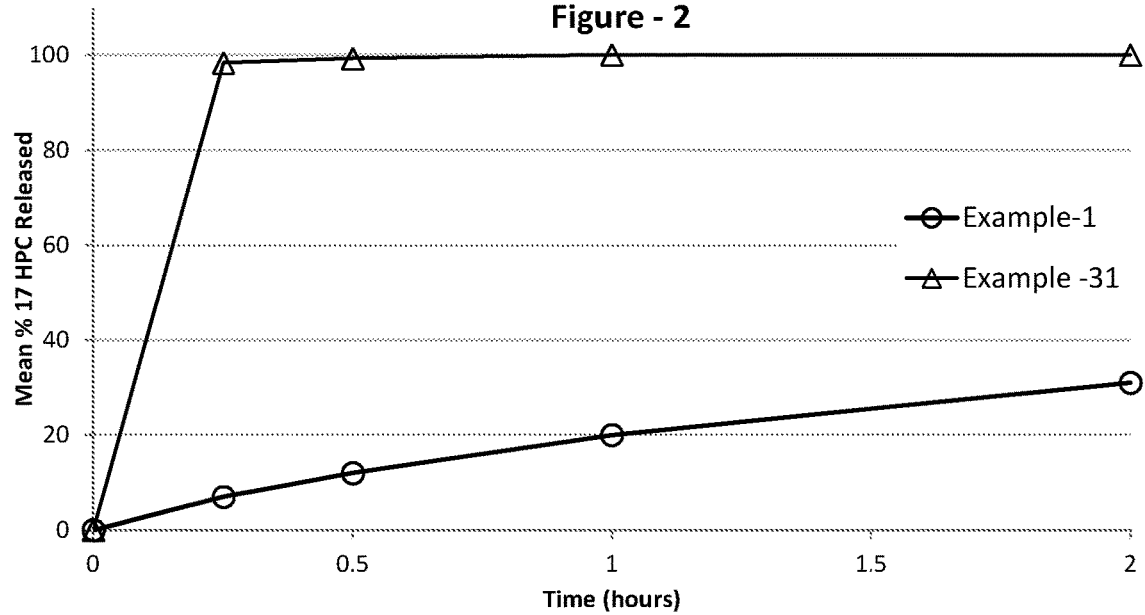

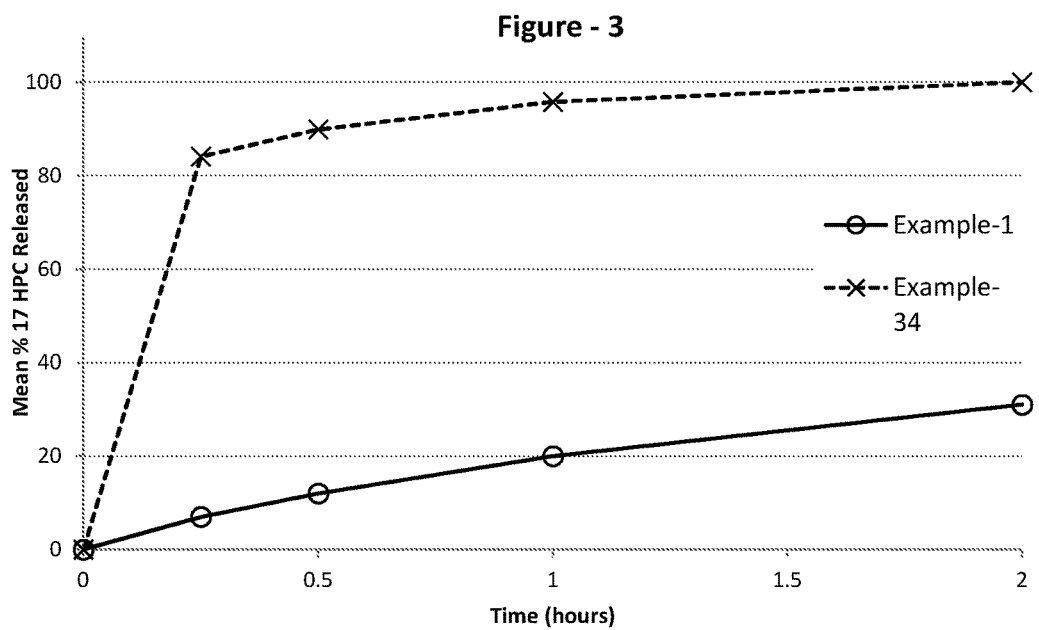

US 10,709,716 B2

17-HYDROXYPROGESTERONE ESTER-CONTAINING ORAL COMPOSITIONS AND RELATED METHODS

PRIORITY DATA

This application is a continuation of U.S. patent application Ser. No. 16/010,188, filed Jun. 15, 2018, which is a continuation of U.S. patent application Ser. No. 15/090,800, filed on Apr. 5, 2016, now issued as U.S. Pat. No. 10,022,384, which is a continuation of U.S. patent application Ser. No. 14/477,771, filed on Sep. 4, 2014, now issued as U.S. Pat. No. 9,358,298, which is a continuation of U.S. patent application Ser. No. 13/193,571, filed on Jul. 28, 2011, now issued as U.S. Pat. No. 8,951,996, each of which is incorporated herein by reference.

FIELD OF THE INVENTION

The present invention relates to 17-hydroxyprogesterone ester containing compositions, oral dosage forms thereof, and associated methods. Accordingly, this invention involves the fields of chemistry, pharmaceutical sciences, medicine and other health sciences.

BACKGROUND OF THE INVENTION 17-alpha hydroxyprogesterone (alternatively hereinafter referred to as 17-hydroxyprogesterone or "17HP") is a C-21 endogenous steroid hormone produced during the syntheses of glucocorticoids and sex steroids. Like progesterone, 17HP is a natural progestagen. It has been isolated from both adrenal glands and corpora lutea. Esters of 17HP are reported to have progestogenic effects and hence, can be used for indications related to pregnancy support as well as non-pregnancy support in both pre- and post-menopausal women. It is reported that 17HP, without esterification, has no progestational activity. However, the synthetic esters of 17HP such 17-hydroxyprogesterone acetate or 17-alpha-hydroxyprogesterone caproate (also referred hereafter as 17 hydroxyprogesterone caproate or 17 HPC) have been shown to exhibit marked progestational activity when administered intramuscularly in animal experiments. 17-Hydroxyprogesterone caproate is a commonly used progestin available for intramuscular injection to prevent Preterm Birth (alternatively hereinafter referred to as "PTB"). This synthetic caproate ester is reportedly inactive when given by mouth but works as a long-acting progestin when administered intramuscularly. The metabolism of 17HP and the metabolism of 17-hydroxyprogesterone caproate in the human female are not yet fully established. Data from humans and animals indicate that intramuscularly administered 17-hydroxyprogesterone caproate has more potent progestational effect on endometrium and is longer lasting than progesterone (alternatively hereinafter referred to as "P"). This may be due to more avid binding of 17-hydroxyprogesterone caproate to the progesterone receptors (alternatively referred to hereinafter as "PR") and placental glucocorticoid receptors (alternatively referred to hereinafter as "GR") that could prevent an increase of placental corticotropin releasing hormone which is associated with onset of labor. 17-hydroxyprogesterone caproate is reportedly effective in providing luteal support in patients undergoing IVF-Embryo Transfer Cycles.

PTB is medically defined as delivery from 20 to 36 weeks of gestation. According to the 2009 Center for Disease Control Report, PTB occurs in about 12.3% of births in the US alone translating to about half a million PTBs annually. Spontaneous PTB accounts for approximately 70-80% of PTB. Of all the pregnancies in the US, one out of every eight live-born infants is born preterm representing an increase of >18% since 1990. Late pre-term birth between 35-36 weeks of gestation contributes to more than half of all PTBs. PTB is the primary cause of neonatal morbidity and mortality. Mortality risk is three fold higher at 35-36 weeks and morbidities such as respiratory distress requiring oxygen, temperature instability, hypoglycemia, jaundice, attention deficit disorders, cerebral palsy, developmental delay, etc. are quite common. PTB related time and costs in intensive care are a major health, social and economic issue with an average cost of PTB delivery amounting to up to 10× that of normal delivery.

Major risk factors implicated in PTB are as follows: History of previous spontaneous PTB (past obstetrics history), cervical length (<2.5 cm at mid pregnancy), presence of fetal fibronectin in vaginal secretions; multiple gestation, low maternal Body Mass Index (BMI), maternal race; maternal age (<17 and >35 years), and smoking. The prior history of at least one PTB is a good indicator of future occurrence potential with 17-50% recurrence potential and 28-70% recurrence potential with two previous PTBs. Benefits of prolonging pregnancy to full term with therapeutic intervention include improved child survival as a function of gestational age, and reduced neonatal hospital stay.

Intramuscular injection of 17-hydroxyprogesterone caproate is available for reducing the risk of PTB in women with singleton pregnancy and history of single spontaneous PTB. The injection marketed as Makena (250 mg 17-hydroxyprogesterone caproate in 1 mL) mandates regular visits to the doctor's office, as the typical treatment cycle consists of 16-20 weeks of injection repeated every week. This therapy regimen could result increasing the patient's distress and/or anxiety in addition to increasing the repeated travel risks for the patient and fetus. The injection therapy's interferences with the personal and family activities and disruption in professional life are also a major disadvantage.

In addition, adverse events with injection of 17-hydroxyprogesterone caproate (e.g. Makena®) at once weekly (every 7 days) the injection site reactions (~45%) such as urticaria, pruritis, swelling, nodule formation and pain at the site of injection have been reported as significant.

Esters of hydroxy progesterone such as acetate, caproate, undecanoate are more lipophilic than hydroxy progesterone. The active substance (17-hydroxyprogesterone caproate) in Makena® is known to be extremely insoluble in water (<20 ng/mL), and very lipophilic with C log P of about 5.7. Moreover, 17-hydroxyprogesterone caproate has the potential to be metabolized in the presence of fetal and adult hepatocytes and is a substrate for cytochrome inactivation such as CYP3A4 which is overly expressed in pregnant women (~40% upregulation). Due to its extremely low water solubility and a potential to be susceptible for first pass hepatic inactivation oral delivery of long chain esters of 17HP has remained a challenge. It is reported that there is no oral activity with 17 hydroxyprogesterone caproate, an ester of 17 HP, (Saxton D J et. al. *Reproductive Biology and Endocrinology* 2004, 2:80; Greene M F, *N JEM* 348:2453-2455). This could be likely due to very poor or no oral bioavailability of 17 HPC. Although much desired, to date the development of an orally active composition of long chain ester of hydroxyl progesterone remains a significant unmet need. In addition, development of dosage forms that enable administration of lesser number of dosage units per dose and/or at reduced frequency per day is most often desirable.

SUMMARY OF THE INVENTION

It has now been surprisingly found that esters of 17HP can be effectively delivered orally to mammals. The pharmaceutical oral compositions and dosage forms of the present inventions can provide effective bioavailability of an ester of 17HP. Further, the compositions and/or dosage forms disclosed herein provide effective release enhancement for 17 HP esters. We have also surprisingly found that an ester of 17HP can be formulated into oral compositions and oral dosage forms thereof with higher percent w/w loading of the ester. For example, we have found that when one or more solubilizing agents such as for example, benzyl alcohol, benzyl benzoate etc., is incorporated in the composition, a significant amount (i.e. greater than 12% w/w) of the ester of 17HP can be solubilized in the composition or dosage form. The increased drug loading in the compositions and dosage forms of the current inventions, can provide avid advantages including but not limited to reduced size or volume of the unit dosage (i.e. tablet, capsule, syrup, elixir, beverage, etc.), reduced number of dosage units to be taken per single administration, improved patient compliance etc., because patients typically can take fewer number of dosage units per day in order to get a sufficient dose to provide the desired efficacy. In a separate aspect, it was also surprisingly found that an effective bioavailability of the ester of 17HP can be provided by the compositions of the current inventions which when dispersed in an aqueous medium, provide clear or colloidal to hazy or unclear dispersions having partially or fully solubilized drug in the dispersions.

It was also found that the compositions of current invention enable production of solid dosage forms such as tablets, caplets, granules, beads, particulates etc., which can solve the drawbacks of having the 17HP ester in a liquid solution form in the dosage unit. This eliminates a number of undesirable inconveniences, such as specialized manufacturing process and/or equipment, poor chemical and/or physical stability of the ester typical to liquid solutions due to the nature of the ester or solvents used, and so-on.

All the oral dosage forms of the present inventions have the drug in the form of solution, suspension, particulates, etc., can be produced by conventional methods of processing and manufacture known in the art.

The present invention provides for compositions and oral dosage forms containing esters of 17HP as well as related methods. The compositions and oral dosage forms can be formulated to include a therapeutically effective amount of an ester of 17HP and a pharmaceutically acceptable carrier. In one embodiment, a pharmaceutically acceptable oral dosage form for pregnancy support and non-pregnancy support is provided. The pharmaceutically acceptable oral dosage can include a therapeutically effective amount of an ester of 17HP and a pharmaceutically acceptable carrier. The oral dosage form can, when measured using a USP Type-II dissolution apparatus in 900 mL of deionized water with 0.5% (w/v) of sodium lauryl sulfate at 50 RPM at 37° C., release at least 20 wt % of the dose of the ester of 17HP after 60 minutes.

In yet a further embodiment, a pharmaceutically acceptable oral dosage form for pregnancy or non-pregnancy support is provided. The pharmaceutically acceptable oral dosage can include a therapeutically effective amount of an ester of 17HP and a pharmaceutically acceptable carrier. The oral dosage form can, when measured using a USP Type-II dissolution apparatus in 900 mL of deionized water with 0.5% (w/v) of sodium lauryl sulfate at 50 RPM at 37° C., release at least 20 wt % more 17HP ester after 60 minutes than an equivalently dosed oral dosage form without the carrier.

In some aspects, the oral dosage forms of the present invention can be used to treat pregnant female subjects who are at risk of preterm birth. Such methods of treatment may include the step of orally administering to the female subject the oral pharmaceutical composition. In some aspects, the dosage amount is an amount sufficient to provide an intended therapeutic effect. In another embodiment, the oral dosage forms can be administered to subjects in need thereof. The administration of the oral dosage form can treat at least one condition selected from preterm labor, preterm birth, infertility and miscarriage. The conditions and the relative treatment can be based on their primary and secondary outcome measurements associated with the administration of the ester of 17HP.

BRIEF DESCRIPTION OF THE DRAWINGS

FIG. 1 is a plot of the in vitro release profile of a 17-hydroxyprogesterone caproate containing oral dosage form in accordance with a certain embodiment of the present invention compared to a carrier-free dose of 17-hydroxyprogesterone caproate.

FIG. 2 is a plot of the in vitro release profiles of 17-hydroxyprogesterone containing oral dosage forms in accordance with a certain embodiment of the present invention.

FIG. 3 is a plot of the in vitro release profiles of 17-hydroxyprogesterone containing oral dosage forms in accordance with a certain embodiment of the present invention.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

Before the present oral dosage forms and methods for the delivery and use of 17-hydroxyprogesterone esters are disclosed and described, it is to be understood that this invention is not limited to the particular process steps and materials disclosed herein, but is extended to equivalents thereof, as would be recognized by those ordinarily skilled in the relevant arts. It should also be understood that terminology employed herein is used for the purpose of describing particular embodiments only and is not intended to be limiting.

It should be noted that, the singular forms "a," "an," and, "the" include plural referents unless the context clearly dictates otherwise. Thus, for example, reference to "an excipient" includes reference to one or more of such excipients, and reference to "the carrier" includes reference to one or more of such carriers.

Definitions

As used herein, "drug," "active agent," "bioactive agent," "pharmaceutically active agent," "therapeutically active agent" and "pharmaceutical," may be used interchangeably to refer to an agent or substance that has measurable specified or selected physiologic activity when administered to a subject in a significant or effective amount. It is to be understood that the term "drug" is expressly encompassed by the present definition as many drugs and prodrugs are known to have specific physiologic activities. These terms of art are well-known in the pharmaceutical and medicinal arts. Further, when these terms are used, or when a particular active agent is specifically identified by name or category, it is understood that such recitation is intended to include the active agent per se, as well as pharmaceutically acceptable salts, esters or compounds significantly related thereto, including without limitation, prodrugs, active metabolites, isomers, and the like.

As used herein, the term "recurrent" is used to refer to a repeat or re-occurrence of at least one incidence like "miscarriage", "preterm birth" or "preterm labor" or "multifetal gestation" or any like medical situation in reference with or without same partner, with or without previous live birth.

As used herein, the term "treatment" when used in conjunction with the administration of a 17-hydroxyprogesterone ester, refers to the administration of the 17-hydroxyprogesterone ester to subjects who are either asymptomatic or symptomatic. In other words, "treatment" can refer to the act of reducing or eliminating a condition (i.e. symptoms manifested), or it can refer to prophylactic treatment, (i.e. administering to a subject not manifesting symptoms in order to prevent their occurrence). Such prophylactic treatment can also be referred to as prevention of the condition, preventative action, preventative measures, etc.

As used herein, the term "ester" represents compounds produced by reaction between acids and alcohols with the elimination of water. As described herein, the term "ester" can also represent the class of organic compounds corresponding to the inorganic salts formed from an organic acid and an alcohol. In one aspect, the "ester of 17-hydroxyprogesterone" can be the caproate ester, but can also represent esters of the longer chain fatty acids such as undecanoic acid and higher, that typically get lymphatically absorbed and avoid first pass hepatic metabolism for improved efficacy or safety.

As used herein, the terms "formulation" and "composition" are used interchangeably and refer to a mixture of two or more compounds, elements, or molecules. In some aspects the terms "formulation" and "composition" may be used to refer to a mixture of one or more active agents with a carrier or other excipients. Furthermore, the term "dosage form" can include one or more formulation(s) or composition(s) provided in a format for administration to a subject. When any of the above terms is modified by the term "oral" such terms refer to compositions, formulations, or dosage forms formulated and intended for oral administration to subjects.

The terms "pharmaceutically acceptable carrier" or "carrier" are used interchangeably and refer to a pharmaceutically acceptable substance that enables a pharmaceutical composition and/or a dosage form of an ester of 17-hydroxyprogesterone. Further, in some aspects, the carrier is an element or ingredient that can be varied for the alteration of release rate and/or extent of the active agent, for example an ester of 17-hydroxyprogesterone, from the composition and/ or the dosage form. In one aspect of the invention, a pharmaceutically acceptable carrier is a compound, or a mixture of compounds, that determines, controls, or contributes, at least in part, to the release of an ester of 17-hydroxyprogesterone from a pharmaceutical oral composition and/or dosage form, when tested using a USP Type II apparatus in about 900 mL of simulated intestinal fluid (according to USP, SIF, without enzyme) having 0.5% w/w sodium lauryl sulfate at about 37° C. and 50 rpm.

In another embodiment, the composition or dosage form provides a release of the ester of 17-hydroxyprogesterone such that when tested using a USP Type II apparatus in about 900 mL of simulated intestinal fluid having 0.5% w/w sodium lauryl sulfate at about 37° C. and 50 rpm, at least 20% more the ester of 17-hydroxyprogesterone is released after the first 60 minutes compared to an equivalent dose an ester of 17-hydroxyprogesterone oral dosage form without the pharmaceutically acceptable carrier. In another particular embodiment, the composition or the dosage form releases at least 40% more of the ester of 17-hydroxyprogesterone after the first 60 minutes compared to an equivalent dose an ester of 17-hydroxyprogesterone oral dosage form without the pharmaceutically acceptable carrier.

It should be noted that the release of the ester of 17-hydroxyprogesterone from the composition or the dosage form can be tested in a suitable solubilizing medium or a non-solubilizing aqueous medium at about 37° C., in a USP Type II apparatus at 50 rpm. For example, aqueous medium can be water, simulated gastric fluid (SGF) with or without enzyme, simulated intestinal fluid (SIF) with or without enzyme, a hydro-alcoholic solution, a surfactant solution and the like. The aqueous medium can be used for the purpose of determining the release rate and/or extent of the ester of 17-hdroxyprogesterone from the compositions or the dosage forms. The aqueous medium can be a non-solubilizing aqueous medium (for example, having low or no surfactant in the medium) for the entire amount of the ester present in the composition or the dosage form. In one embodiment, the non-solubilizing aqueous medium can solubilize about 90% or less of the amount of ester present in the composition or dosage form. In another embodiment, the non-solubilizing aqueous medium can solubilize about 80% or less, about 70% or less, about 60% or less, about 50% or less, about 30% or less, or about 20% or less of the total amount of the ester present in the composition or dosage form.

Conversely, in another embodiment the aqueous medium is capable of solubilizing substantially all of the ester of 17-hydroxyprogesterone present in the composition or dosage form. In one embodiment, the aqueous medium can solubilize at least about 90% of the amount of the ester of 17-hydroxyprogesterone present in the composition or dosage form. In a particular embodiment the aqueous medium can solubilize about 1.5 times or more, about 3 times or more, 5 times or more of the amount of the ester 17-hydroxyprogesteron present in the composition or dosage form.

As used herein, "subject" refers to a mammal that may benefit from the administration of a drug composition or method of this invention. Examples of subjects include humans, and may also include other animals such as horses, pigs, cattle, dogs, cats, rabbits, and aquatic mammals. In one specific aspect, a subject is a human. In another aspect, the subject is a female. In yet another aspect, the oral dosage form of the current invention is for a female requiring pregnancy support.

The term "oral administration" represents any method of administration in which an active agent can be administered by swallowing, chewing, or sucking or drinking an oral dosage form. Such solid or liquid oral dosage forms are traditionally intended to substantially release and or deliver the active agent in the gastrointestinal tract beyond the mouth and/or buccal cavity. Examples of solid dosage forms include conventional tablets, multi-layer tablets capsules, caplets, etc., which do not substantially release the drug in the mouth or in the oral cavity.

As used herein, the terms "release" and "release rate" are used interchangeably to refer to the discharge or liberation of a substance, including without limitation a drug, from the dosage form into a surrounding environment such as an aqueous medium either in vitro or in vivo.

As used herein, the term "lipophilic" when used in combination with both solid and liquid lipophilic additives (alternatively referred to hereinafter as "LA"), refers to additives that "love oil" and generally have poor or no solubility in water. "Lipophilic surfactants" (alternatively referred to hereinafter as "LS") refer to lipophilic additives that have HLB values of 10 or less, preferably between 2 to 10. Conversely, the term "hydrophilic," when used in combination with both solid and liquid hydrophilic additives (alternatively referred to hereinafter as "HA"), refers to additives that "love water", and generally have average or good solubility in water. "Hydrophilic surfactants" (alternatively referred to hereinafter as "HS") are hydrophilic additives that have significant surface active property and that have HLB values of more than 10.

As used herein, the term "lipid" or lipid substance" when used in connection, with various compounds, refers to fatty acid (unless otherwise specified, having chain length greater than $C_6$) or fatty acid esters or glycerides of fatty acid esters, mixtures thereof and derivatives thereof, although not including salts thereof.

In some aspects of the present invention, the release of the drug may be controlled release. As used herein, the term "controlled release" represents the release of the drug from the dosage form according to a predetermined profile. In some aspects, the controlled release selected can be, intermediate, delayed, extended, sustained, pulsatile, gastric, enteric or colonic. In another aspect, combinations of the aforementioned release profiles may be used in order to achieve specific delivery results, such as an immediate release followed by a delayed and/or a sustained release of the active agent.

As used herein, a composition or dosage form provides "immediate release" when greater than about 90% of the drug is released after the first 30 minutes, in a USP simulated gastric fluid (SGF) with or without enzyme.

As used herein, the term "pregnancy support" when used to describe the functionality of the oral compositions or dosage forms of the present invention, can refer to providing exogenous progestational support from inception through birth including, but not limited to preterm birth, preterm labor, and miscarriage. The pregnancy support can provide improved quality of the pregnancy for the pregnant woman, the fetus, or both. Further, pregnancy support can also include increased fertility for a woman trying to become pregnant.

As used herein, the term "non-pregnancy" support when used to describe the functionality of the oral compositions or dosage forms of the present invention, can refer to conditions that require exogenous supplementation of a progestogen agent to a non-pregnant subject, such as a non-pregnant woman, including but not limited to, delaying or preventing the occurrence of undesirable pregnancy, preventing or treating conditions due to progesterone deficiencies such as amenorrhea, fibroids, contraception, postpartum lactation suppression, treatment of dysfunctional uterine bleeding, endometriosis, endometrial hyperplasia, cervical hyperplasia, hormone replacement therapy, treatment of hypoventilation, prevention and treatment of osteoporosis, management of breast, hypothyroidism, migraine headaches, pemporomandibular joint syndrome, catamenial epilepsy, endometrial, and/or renal carcinomas. In one embodiment, the term "non-pregnancy" support when used to describe the functionality of the oral compositions or dosage forms of the present invention can refer to conditions that require exogenous supplementation of the progestogen agent of the invention to a male human for example, to effect contraception, to counter estogenic activity, etc. It should be noted that the present compositions and dosage forms of the ester of the 17-hydroxyprogesterone may be administered alone or in combination with other therapy. In another embodiment, the current invention compositions and dosage forms of the ester of the 17-hydroxyprogesterone may be used to supplement, augment, mitigate, treat, cure or prevent, or for providing prophylaxis in a subject in need thereof.

As used herein, an "effective amount" or a "therapeutically effective amount" of a drug refers to a non-toxic, but sufficient amount of the drug, to achieve therapeutic results in treating a condition for which the drug is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a somewhat subjective decision. The determination of an effective amount is well within the ordinary skill in the art of pharmaceutical sciences and medicine. See, for example, Meiner and Tonascia, "Clinical Trials: Design, Conduct, and Analysis," *Monographs in Epidemiology and Biostatistics*, Vol. 8 (1986), incorporated herein by reference.

As used herein, the term "about" is used to provide flexibility to a numerical range endpoint by providing that a given value may be "a little above" or "a little below" the endpoint. As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, levels and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Invention

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, variants, modifications, and equivalents as may be included within the spirit and scope of the invention as defined by the appended claims.

During pregnancy, it has been shown that serum progestogen, including progesterone and 17-hydroxyprogesterone levels are decreased in the pregnant female in cases of intrauterine death, premature labor, threatened premature labor, premature rupture of membranes, amnionitis and abruption of placenta. As discussed above, it has been discovered that esters of 17-hydroxyprogesterone have potential for use in pregnancy to treat and or prevent the following conditions or occurrences: spontaneous abortion in women who have had previous spontaneous abortion, history of recurrent spontaneous abortion, previous stillbirth, previous premature delivery (<37 weeks), previous premature (<37 weeks) rupture of membranes or PROM, previous pregnancy related hypertension or toxemia, previous abruption of placenta, threatened premature labor or cerclage, multiple pregnancy, primary or secondary infertility, congenital uterine anomaly or any other condition where endogenous progestogen (e.g. progesterone) levels are lower than in normal pregnancy.

Primary and secondary outcome measures can be used to determine the need for and/or the effectiveness of ester of 17-hydroxyprogesterone supplementation therapy for pregnancy related support to a particular subject and its direct or indirect effect on the neonates. Typical primary and secondary outcome measures for preterm birth and preterm labor include, without limitation, Primary Outcome Measures (Maternal):
1. Perinatal mortality
2. Preterm birth (less than 32 weeks' gestation)
3. Preterm birth (less than 34 weeks' gestation)
4. Preterm birth (less than 37 weeks' gestation)
5. Major neuro-developmental handicap at childhood follow up Secondary Outcome Measures (Maternal):
1. Threatened preterm labor
2. Pre-labor spontaneous rupture of membranes
3. Adverse drug reaction
4. Pregnancy prolongation (interval between randomization and birth)
5. Mode of birth
6. Number of antenatal hospital admissions
7. Satisfaction with the therapy
8. Use of tocolysis Secondary Outcome Measures (Infant):
1. Birth before 37 completed weeks
2. Birth before 34 completed weeks
3. Birth before 32 completed weeks
4. Birth before 28 completed weeks
5. Birth weight less than the third centile for gestational age
6. Birth weight less than 2500 grams
7. Apgar score of less than seven at five minutes
8. Respiratory distress syndrome
9. Use of mechanical ventilation
10. Duration of mechanical ventilation
11. Intraventricular hemorrhage—grades III or IV
12. Periventricular leucomalacia
13. Retinopathy of prematurity
14. Retinopathy of prematurity—grades III or IV
15. Chronic lung disease
16. Necrotizing enterocolitis
17. Neonatal sepsis
18. Fetal death
19. Neonatal death
20. Admission to neonatal intensive care unit
21. Neonatal length of hospital stay
22. Teratogenic effects (including virilisation in female infants)

Secondary Outcome Measures (Child):
1. Major sensorineural disability (defined as any of legal blindness, sensorineural deafness requiring hearing aids, moderate or severe cerebral palsy, or developmental delay or intellectual impairment)
2. Developmental delay
3. Intellectual impairment
4. Motor impairment
5. Visual impairment
6. Blindness
7. Deafness
8. Hearing impairment
9. Cerebral palsy
10. Child behavior
11. Child temperament
12. Learning difficulties
13. Growth assessments at childhood follow up (weight, head circumference, length, skin fold thickness)

In-Vitro Fertilization
1. Primary Outcome Measures:
    1.1. Pregnancy Rate
    1.2. Live birth
    1.3. Ongoing pregnancy rate
    1.4. Clinical pregnancy, defined as ultrasound evidence of fetal heart activity at 6-8 weeks of gestation
    1.5. Fetus Vitality measured by heart beat
    1.6. Rate of complete abortion 24-48 hrs after receiving medical treatment for early pregnancy failure.
2. Secondary Outcome Measures:
    2.1. Clinical pregnancy
    2.2. Cycle Cancellation Rates
    2.3. Number of Oocytes Generated
    2.4. Number of Embryos Generated
    2.5. Serum hormonal evaluation
    2.6. Follicular fluid evaluation
    2.7. Peak estradiol level
    2.8. Ampules of gonadotropins required during ovarian stimulation
    2.9. Number of days of ovarian stimulation
    2.10. Number of oocytes retrieved
    2.11. Number of embryos transferred
    2.12. Number of embryos frozen
    2.13. Embryo grade
    2.14. Implantation rate
    2.15. Miscarriage rate
    2.16. Pregnancy outcome
    2.17. rate of complete abortion at one week, time to expulsion of products of conception, correlation of abortion rates to serum 17-hydroxyprogesterone levels and type of pregnancy failure, number of bleeding days and patient satisfaction
    2.18. Ovarian Response [assessed upon completion of the controlled ovarian stimulation and the egg collection procedures]

Miscarriage
1. Primary Outcomes
   1.1. Miscarriage
   1.2. Early miscarriage up to 12 weeks
   1.3. Miscarriage later than 12 weeks and less than 23 weeks
   1.4. Cytokine ratio IFN/IL-10
   1.5. Clinical pregnancy rate at 8 weeks and 12 weeks of pregnancy
2. Secondary Outcomes
   2.1. Mother
      a. Pain relief (threatened miscarriage)
      b. Severity of 'morning sickness'—intensified headache
      c. nausea, breast tenderness
      d. reported thromboembolic events
      e. Thrombolytic events
      f. depression;
      g. admission to special care unit
      h. subsequent fertility.
      i. PIBF level
      j. Uterine contraction frequency
   2.2. Child
      a. Preterm birth;
      b. stillbirth;
      c. neonatal death;
      d. low birthweight less than 2500 g
      e. fetal genital abnormalities;
      f. teratogenic effects (impairing normal fetal development);
      g. admission to special care unit.
   2.3. General
      a. Intrauterine fetal death
      b. Still birth
      c. Fetal
      d. Exploratory analysis of pregnancy outcome by monitoring biochemical and clinical pregnancy parameters, weekly evaluation of serum progesterone
      e. live birth rate, cycle cancellation rate, rate of spontaneous abortion, rate of biochemical pregnancy, rate of ectopic pregnancy Several biomarkers have been implicated in predicting preterm birth (PTB). Among symptomatic women, the likelihood ratio (LR+) for the prediction of PTB is known to be greater than 10 using amniotic fluid (AF) interleukin-6 (IL-6), AF *Ureaplasma urealyticum*, as well as a multi-marker consisting of cervical IL-6, cervical IL-8, and cervical length (CL). The LR+ is also known to be between 5 and 10 for serum C-reactive protein (CRP). An LR+ between 2.5 and 5 was recorded for serum corticotropin-releasing hormone (CRH), cervical IL-6, serum relaxin.

In asymptomatic women, AFU urealyticum and a multi-marker consisting of five individual markers [fFN, CL, serum alpha-fetoprotein (AFP), serum alkaline phosphatase, and serum granulocyte colony-stimulating factor (G-CSF)] predict PTB with an LR+ greater than 10. The LR+ was between 5 and 10 for serum relaxin and CL. LRs+ recorded for serum alkaline phosphatase, salivary estriol, serum CRH, serum G-CSF, cervical IL-6, AF IL-6, cervical fFN, AFP, and chlamydia all ranged between 2.5 and 5. Finally, an LR+ below 2.5 has been documented for serum ferritin, serum CRP, BV, and cervical ferritin.

Miscarriages and possible miscarriages can be categorized in several ways: A) threatened or possible miscarriage—when any bleeding from the uterus occurs before 20 weeks, but the cervix is closed and the fetus is alive; B) Inevitable abortion or miscarriage (inevitable—meaning it cannot be stopped, particularly if there is bleeding from the uterus and the cervix is opening prior to 20 weeks, but neither the fetus nor placenta have passed out of the woman's body)—the membranes around the fetus may or may not have ruptured (broken); C) Incomplete abortion or miscarriage—when a portion of the fetus or placenta has passed out of the uterus prior to 20 weeks gestation while some of the placenta or fetus remains in the uterus; D) Complete miscarriage—complete expulsion of all the membranes around the fetus and the placenta and the cervix closes prior to 20 weeks; E) Missed abortion or miscarriage—death of the fetus prior to 20 weeks gestation with neither the fetus nor the placenta having been expelled from the uterus; F) Recurrent miscarriage—a woman is said to have recurrent miscarriage after she has already had two or more miscarriages in a row; G) Blighted ovum or anembryonic gestation—occurs when a gestational sac forms inside the uterus, but no fetus is present after seven weeks.

Threatened miscarriage, as demonstrated by low endogenous progesterone or 17-hydroxyprogesterone, or vaginal bleeding with or without abdominal cramps within 26 weeks of conception, is a common complication of pregnancy. It occurs in about 20% of recognized pregnancies. Risk of miscarriage is increased in older women and those with a history of miscarriage.

It has been shown that low serum levels of progestogen (progesterone or 17 HP) or human chorionic gonadotropin (hCG) are a risk factor for miscarriage. Threatened miscarriage causes considerable stress and anxiety for a pregnant woman. Because esters of 17-hydroxyprogesterone interact with the progesterone receptor, it is believed that treatment with esters of 17-hydroxyprogesterone can be designed based on progesterone levels. One diagnostic criterion is low serum progesterone, but levels vary widely during early pregnancy and any later decline may be attributed to a dysfunctioning placenta. Nevertheless, luteal support is widely used for the management of threatened miscarriage. First trimester pregnancies show risk of miscarriage with declining serum progesterone levels. Levels of <5 ng/ml were associated with a spontaneous miscarriage in 86% of cases compared with only 8% at levels of 20-25 ng/ml. A threshold value of 14 ng/ml has been reported to differentiate between the viable and non-continuing pregnancies. Other maternal serum biomarkers such as Tumor marker CA-125, Inhibin A, Anandamide and progesterone induced blocking factor (PIBF) are also good indicators of miscarriage risk.

In one embodiment, the compositions of the present invention are intended to provide an increase in the baseline endogenous progesterone and/or 17-hydroxyprogesterone. In a particular embodiment the increase in the baseline endogenous progesterone can be greater than 10%. Progestogens also have a direct pharmacological effect by reducing the synthesis of prostaglandins, thereby relaxing uterine smooth musculature and preventing inappropriate contractions that may result in miscarriage.

Although the oral dosage forms and methods of the present invention can be used in most female subjects, patients most suitable for receiving oral 17-hydroxyprogesterone ester of this invention are the ones that have one or more of the following conditions, symptoms, and/or needs: 1) are in need of an anti-inflammatory; 2) are progesterone deficient with base line progesterone in early (first trimester) pregnancy of $C_{avg}$<14 ng/ml or baseline progesterone levels, $C_{avg}$ of less than 50 ng/ml in late (second and third trimester) pregnancy; 3) have genetic variation of the SERPINH1 gene that cause to produce a reduced amount of the protein, collagen, which may lead to weakened fetal membranes; 4)

have a genetic variant of the Prolylcarboxypeptidase gene associated with preeclampsia; 5) have certain bacterial infections (bacterial vaginosis) including *Ureaplasma urealyticum, Mycoplasma hominis, Gardnerella vaginalis,* and *Peptostreptococcus* and *Bacteroides* species; 6) have abnormal amniotic fluid metabolome (the sum of all metabolic processes occurring in the amniotic fluid) indicating risk for prematurity; 7) have had above average total phthalate exposure; 8) abnormal prepregnancy body mass index; 9) have inflammatory milieu of the vagina in early pregnancy; 10) have increased maternal plasma urocortin levels; 11) show increased uterine activity as noted by Home Uterine Activity Monitoring; 12) test positive to salivary estriol levels predicting preterm delivery; 13) show alarming fetal Fibronectin Screening (fFS) results; 14) show unusual cervical shortening relative to gestational age as measured by cervical ultrasonography, or transvaginal ultrasound or digital examination with/without use of Cervilenz™; 15) show unusual maternal serum bio markers such as Tumour marker CA-125, or Inhibin A, or Anandamide or Progesterone Induced Blocking factor (PIBF); 16) have unbalanced ratio of Th-1 cytokines to Th-2 cytokines such as IFN to IL-10.

Besides maintaining pregnancy, other potential uses of the ester of 17-hydroxyprogesterone containing oral dosage forms of the present invention include, but are not limited to: a) preventing estrogen dominance; b) stimulating new bone formation and prevent/reverse osteoporosis; c) providing the precursor for adrenal cortex hormones (corticosteroids); d) treating variety of skin problems such as acne in adult women, seborrhea, rosacea, psoriasis, and keratosis; e) promoting myelin sheath production to protect nerve fibers and speed nerve signals; f) managing depression that accompany PMS, menopause, postpartum depression, etc.; g) protecting from brain/spinal cord injury, stroke, and/or hemorrhage.

In one embodiment, the present invention provides for oral dosage forms containing esters of 17-hydroxyprogesterone as well as related methods. The oral dosage forms can be formulated for pregnancy support and can include a therapeutically effective amount of an ester of 17-hydroxyprogesterone and a pharmaceutically acceptable carrier. The oral dosage form can, when measured using a USP Type-II dissolution apparatus in 900 mL of deionized water with 0.5 (w/v) of sodium lauryl sulfate at 50 RPM at 37° C., release at least 20 wt % of the dose of the ester of 17-hydroxyprogesterone after 60 minutes. In yet a further embodiment, the oral dosage form can, when measured using a USP Type-II dissolution apparatus in 900 mL of deionized water with 0.5 (w/v) of sodium lauryl sulfate at 50 RPM at 37° C., release at least 20 wt % more 17-hydroxyprogesterone ester after 60 minutes than an equivalently dosed oral dosage form without the carrier.

A number of 17-hydroxyprogesterone esters can be used in the compositions and oral dosages of the present invention. Examples of specific acceptable esters of 17-hydroxyprogesterone include without limitation, acetate esters of 17-hydroxyprogesterone, caproate esters of 17-hydroxyprogesterone, undecanoate esters of 17-hydroxyprogesterone, and the like and combinations thereof. Other pharmacologically active and acceptable esters of 17-hydroxyprogesterone may also be prepared and used in accordance with the embodiments of the present invention so long as they provide the desired support in pregnancy and/or non-pregnancy conditions.

The ester of 17-hydroxyprogesterone can be present in the compositions and oral dosage forms of the present disclosure in a variety of forms. In one embodiment, the ester of 17-hydroxyprogesterone can be present in particulate form.

In one embodiment, the ester of 17-hydroxyprogesterone can be present in particulate form. The particulate form can have a mean diameter of about 50 μm or less. The particulate form can have a mean diameter of about 25 μm or less. In another embodiment, the particulate form can have a mean diameter of about 1 μm or less. In another embodiment, the ester of 17-hydroxyprogesterone can be present in a fully solubilized form. In another embodiment, the ester of 17-hydroxyprogesterone can be present in a partially solubilized form. In another embodiment, a portion of the ester of 17-hydroxyprogesterone present in the composition and/or dosage form can be present in particulate or unsolubilzied form. In some embodiments, the ester of 17-hydroxyprogesterone can be present in both solubilized form as well as in particulate form.

In some embodiments, the carrier of the compositions or oral dosage forms of the present invention can act to facilitate the delivery, release, and/or bioavailability of the ester of 17-hydroxyprogesterone. In certain aspects, the carrier can be one or a mixture of two or more compounds. The carrier can include at least one of a lipophilic and/or a hydrophilic component additive. The lipophilic and hydrophilic additives that can be used in the compositions of the invention can be selected from a variety of classes of the pharmaceutical aids including, but not limited to, absorbents, acids, adjuvants, anticaking agent, antitacking agents, antifoamers, anticoagulants, antimicrobials, antioxidants, antiphlogistics, astringents, antiseptics, bases, binders, bufferants, chelating agents, sequestrants, celluloses, coagulants, coating agents, colorants, dyes, pigments, complexing agents, crystal growth regulators, denaturants, desiccants, drying agents, dehydrating agents, diluents, disintegrants, dispersants, emollients, emulsifiers, encapsulants, enzymes, extenders, fillers, flavor masking agents, flavorants, fragrances, gelling agents, glidants hardeners, stiffening agents, humectants, lubricants, moisturizers, pH control agents, plasticizers, soothing agents, demulcents, retarding agents, spreading agents, stabilizers, suspending agents, sweeteners, thickening agents, consistency regulators, surfactants, opacifiers, polymers, preservatives, antigellants, rheology control agents, softeners, solubilizers; solvents tonicifiers, viscosity modulators UV absorbers, or combinations thereof. In some embodiments additives from multiple classes or types can be used.

Non-limiting examples of compounds that can form all or a part of the carrier are set forth in the following lists which have been organized in general categories. It is to be understood that the categories are not intended to limit the particular carrier compounds, but are simply present for ease of organization and presentation. With this in mind, example carrier compounds can include one or more of the following:

Triglycerides such as Aceituno oil; Almond oil; Arachis oil; Babassu oil; Blackcurrant seed oil; Borage oil; Canola oil (Lipex 108 (Abitec)); Castor oil; Cocoa butter; Coconut oil (Pureco 76 (Abitec)); Coffee seed oil); Corn oil; Cottonseed oil; Crambe oil; Cuphea species oil; Evening primrose oil; Grapeseed oil; Groundnut oil; Hemp seed oil; Illipe butter; Kapok seed oil; Linseed oil; Menhaden oil; Mowrah butter; Mustard seed oil; Oiticica oil; Olive oil; Palm oil; Palm kernel oil; Peanut oil; Poppy seed oil; Rapeseed oil; Rice bran oil; Safflower oil; Sal fat; Sesame oil; Shark liver oil; Shea nut oil; Soybean oil; Stillingia oil; Sunflower oil; Tall oil; Tea sead oil; Tobacco seed oil; Tung oil (China wood oil): Vernonia oil; Wheat germ oil; Hydrogenated castor oil (Castorwax); Hydrogenated coconut oil (Pureco 100 (Abitec)); Hydrogenated cottonseed oil (Dritex C (Abitec)); Hydrogenated palm oil (Dritex PST (Abitec);

Softisan154 (Huls)); Hydrogenated soybean oil (Sterotex HM NF (Abitec); Dritex S (Abitec)); Hydrogenated vegetable oil (Sterotex NF (Abitec): Hydrokote M (Abitec)); Hydrogenated cottonseed and caster oil (Sterotex K (Abitec)); Partially hydrogenated soybean oil (Hydrokote AP5 (Abitec)); Partially soy and cottonseed oil (Apex B (Abitec)); Glyceryl tributyrate (Sigma); Glyceryl tricaproate (Sigma); Glyceryl tricaprylate (Sigma); Glyceryl tricaprate (Captex 1000 (Abitec)); Glyceryl trundecanoate (Captex 8227 (Abitec)); Glyceryl trilaurate (Sigma); Glyceryl trimyristate (Dynasan 114 (Huls)); Glyceryl tripalmitate (Dynasan 116 (Huls)); Glyceryl tristearate (Dynasan 118 (Huls)); Glyceryl triarcidate (Sigma); Glyceryl trimyristoleate (Sigma); Glyceryl tripalmitoleate (Sigma); Glyceryl trioleate (Sigma); Glyceryl trilinoleate (Sigma); Glyceryl tricaprylate/caprate (Captex 300 (Abitec); Captex 355 (Abitec); Miglyol 810 (Huls); Miglyol 812 (Huls)); Glyceryl tricaprylate/caprate/laurate (Captex 350 (Abitec)); Glyceryl tricaprylate/caprate/linoleate (Captex 810 (Abitec); Miglyol 818 (Huls)); Glyceryl tricaprylate/caprate/stearate (Softisan 378 (Huls); (Larodan); Glyceryl tricaprylate/laurate/stearate (Larodan); Glyceryl 1,2-caprylate-3-linoleate (Larodan); Glyceryl 1,2-caprate-3-stearate (Larodan); Glyceryl 1,2-laurate-3-myristate (Larodan); Glyceryl 1,2-myristate-3-laurate (Larodan); Glyceryl 1,3-palmitate-2-butyrate (Larodan); Glyceryl 1,3-stearate-2-caprate (Larodan); Glyceryl 1,2-linoleate-3-caprylate (Larodan), mixtures and derivatives thereof. Fractionated triglycerides, modified triglycerides, synthetic triglycerides, and mixtures of triglycerides are also within the scope of the invention.

PEG-Fatty Acid Monoester Surfactants (listed as compound name (common commercial product name (supplier) (HLB)): PEG 4-100 monolaurate (Crodet L series (Croda) (>9)); PEG 4-100 monooleate (Crodet O series (Croda) (>8)); PEG 4-100 monostearate (Crodet S series (Croda), Myrj Series (Atlas/ICI) (>6)); PEG 400 distearate (Cithrol 4DS series (Croda) (>10)); PEG 100, 200, 300 monolaurate (Cithrol ML series (Croda) (>10)); PEG 100, 200, 300 monooleate (Cithrol MO series (Croda) (>10)); PEG 400 dioleate (Cithrol 4DO series (Croda) (>10)); PEG 400-1000 monostearate (Cithrol MS series (Croda) (>10)); PEG-1 stearate (Nikkol MYS-1EX (Nikko), Coster K1 (Condea) (2)); PEG-2 stearate (Nikkol MYS-2 (Nikko) (4)); PEG-2 oleate (Nikkol MYO-2 (Nikko) (4.5)); PEG-4 laurate (Mapeg® 200 ML (PPG), Kessco® PEG 200 ML (Stepan), LIPOPEG 2 L (LIPO Chem.) (9.3)); PEG-4 oleate (Mapeg® 200 MO (PPG), Kessco® PEG 200 MO (Stepan) (8.3)); PEG-4 stearate (Kessco® PEG 200 MS (Stepan), Hodag 20 S (Calgene), Nikkol MYS-4 (Nikko) (6.5)); PEG-5 stearate (Nikkol TMGS-5 (Nikko) (9.5)); PEG-5 oleate (Nikkol TMGO-5 (Nikko) (9.5)); PEG-6 oleate (Algon OL 60 (Auschem SpA), Kessco® PEG 300 MO (Stepan), Nikkol MYO-6 (Nikko), Emulgante A6 (Condea) (8.5)); PEG-7 oleate (Algon OL 70 (Auschem SpA) (10.4)); PEG-6 laurate (Kessco® PEG300 ML (Stepan) (11.4)); PEG-7 laurate (Lauridac 7 (Condea) (13)); PEG-6 stearate (Kessco® PEG300 MS (Stepan) (9.7)); PEG-8 laurate (Mapeg® 400 ML (PPG), LIPOPEG 4DL (Lipo Chem.) (13)); PEG-8 oleate (Mapeg® 400 MO (PPG), Emulgante A8 (Condea) (12)); PEG-8 stearate (Mapeg® 400 MS (PPG), Myrj 45 (12)); PEG-9 oleate (Emulgante A9 (Condea) (>10)); PEG-9 stearate (Cremophor S9 (BASF) (>10)); PEG-10 laurate (Nikkol MYL-10 (Nikko), Lauridac 10 (Croda) (13)); PEG-10 oleate (Nikkol MYO-10 (Nikko) (11)); PEG-12 stearate (Nikkol MYS-10 (Nikko), Coster K100 (Condea) (11)); PEG-12 laurate (Kessco® PEG 600 ML (Stepan) (15)); PEG-12 oleate (Kessco® PEG 600 MO (Stepan) (14)); PEG-12 ricinoleate (CAS #9004-97-1) (>10)); PEG-12 stearate (Mapeg® 600 MS (PPG), Kessco® PEG 600 MS (Stepan) (14)); PEG-15 stearate (Nikkol TMGS-15 (Nikko), Koster K15 (Condea) (14)); PEG-15 oleate (Nikkol TMGO-15 (Nikko) (15)); PEG-20 laurate (Kessco® PEG 1000 ML (Stepan) (17)); PEG-20 oleate (Kessco® PEG 1000 MO (Stepan) (15)); PEG-20 stearate (Mapeg® 1000 MS (PPG), Kessco® PEG 1000 MS (Stepan), Myrj 49 (16)); PEG-25 stearate (Nikkol MYS-25 (Nikko) (15)); PEG-32 laurate (Kessco® PEG 1540 ML (Stepan) (16)); PEG-32 oleate (Kessco® PEG 1540 MO (Stepan) (17)); PEG-32 stearate (Kessco® PEG 1540 MS (Stepan) (17)); PEG-30 stearate (Myrj 51 (>10)); PEG-40 laurate (Crodet L40 (Croda) (17.9)); PEG-40 oleate (Crodet O40 (Croda) (17.4)); PEG-40 stearate (Myrj 52, Emerest® 2715 (Henkel), Nikkol MYS-40 (Nikko) (>10)); PEG-45 stearate (Nikkol MYS-45 (Nikko) (18)); PEG-50 stearate (Myrj 53 (>10)); PEG-55 stearate (Nikkol MYS-55 (Nikko) (18)); PEG-100 oleate (Crodet O-100 (Croda) (18.8)); PEG-100 stearate (Myrj 59, Ariacel 165 (ICI) (19)); PEG-200 oleate (Albunol 200 MO (Taiwan Surf) (>10)); PEG-400 oleate (LACTOMUL (Henkel), Albunol 400 MO (Taiwan Surf) (>10)); PEG-600 oleate (Albunol 600 MO (Taiwan Surf) (>10)); and combinations thereof.

PEG-Fatty Acid Diesters (listed as compound name (common commercial product name (supplier) (HLB)): PEG-4 dilaurate (Mapeg®200 DL (PPG), Kessco® PEG 200 DL (Stepan), LIPOPEG 2-DL (Lipo Chem.) (7)); PEG-4 dioleate (Mapeg® 200 DO (PPG), (6)); PEG-4 distearate (Kessco® 200 DS (Stepan) (5)); PEG-6 dilaurate (Kessco® PEG 300 DL (Stepan) (9.8)); PEG-6 dioleate (Kessco® PEG 300 DO (Stepan) (7.2)); PEG-6 distearate (Kessco® PEG 300 DS (Stepan) (6.5)); PEG-8 dilaurate (Mapeg® 400 DL (PPG), Kessco® PEG 400 DL (Stepan), LIPOPEG 4 DL (Lipo Chem.) (11)); PEG-8 dioleate (Mapeg® 400 DO (PPG), Kessco® PEG 400 DO (Stepan), LIPOPEG 4 DO (Lipo Chem.) (8.8)); PEG-8 distearate (Mapeg® 400 DS (PPG), CDS 400 (Nikkol) (11)); PEG-10 dipalmitate (Polyaldo 2PKFG (>10)); PEG-12 dilaurate (Kessco® PEG 600 DL (Stepan) (11.7)); PEG-12 distearate (Kessco® PEG 600 DS (Stepan) (10.7)); PEG-12 dioleate (Mapeg® 600 DO (PPG), Kessco® 600 DO (Stepan) (10)); PEG-20 dilaurate (Kessco® PEG 1000 DL (Stepan) (15)); PEG-20 dioleate (Kessco® PEG 1000 DO (Stepan) (13)); PEG-20 distearate (Kessco® PEG 1000 DS (Stepan) (12)); PEG-32 dilaurate (Kessco® PEG 1540 DL (Stepan) (16)); PEG-32 dioleate (Kessco® PEG 1540 DO (Stepan) (15)); PEG-32 distearate (Kessco® PEG 1540 DS (Stepan) (15)); PEG-400 dioleate (Cithrol 4DO series (Croda) (>10)); PEG-400 distearate (Cithrol 4DS series (Croda) (>10)); and combinations thereof.

PEG-Fatty Acid Mono- and Di-ester Mixtures (listed as compound name (common commercial product name (supplier) (HLB)): PEG 4-150 mono, dilaurate (Kessco® PEG 200-6000 mono, dilaurate (Stepan))); PEG 4-150 mono, dioleate (Kessco® PEG 200-6000 mono, dioleate (Stepan))); PEG 4-150 mono, distearate (Kessco® 200-6000 mono, distearate (Stepan)), and combinations thereof.

Polyethylene Glycol Glygerol Fatty Acid Esters (listed as compound name (common commercial product name (supplier) (HLB)): PEG-20 glyceryl laurate (Tagat® L (Goldschmidt) (16)); PEG-30 glyceryl laurate (Tagat L2 (Goldschmidt) (16)); PEG-15 glyceryl laurate (Glycerox L series (Croda) (15)); PEG-40 glyceryl laurate (Glycerox L series (Croda) (15)); PEG-20 glyceryl stearate (Capmul® EMG (ABITEC), (13)); (Aldo® MS-20 KFG (Lonza))); PEG-20 glyceryl oleate (Tagat® O (Goldschmidt) (>10)); PEG-30 glyceryl oleate (Tagat® O2 (Goldschmidt) (>10)); and combinations thereof.

Alcohol-oil Transesterification Products: (listed as compound name (common commercial product name (supplier) (HLB)): PEG-3 castor oil (Nikkol CO-3 (Nikko) (3)); PEG-5, 9, and 16 castor oil (ACCONON CA series (ABITEC) (6-7)); PEG-20 castor oil (Emalex C-20 (Nihon Emulsion), Nikkol CO-20 TX (Nikko) (11)); PEG-23 castor oil (Emulgante EL23 (>10)); PEG-30 castor oil (Emalex C-30 (Nihon Emulsion), Alkamuls® EL 620 (Rhone-Poulenc), Incrocas 30 (Croda) (11)); PEG-35 castor oil (Cremophor EL and EL-P (BASF), Emulphor EL, Incrocas-35 (Croda), Emulgin RO 35 (Henkel))); PEG-38 castor oil (Emulgante EL 65 (Condea))); PEG-40 castor oil (Emalex C-40 (Nihon Emulsion), Alkamuls® EL 719 (Rhone-Poulenc) (13)); PEG-50 castor oil (Emalex C-50 (Nihon Emulsion) (14)); PEG-56 castor oil (Eumulgin® PRT 56 (Pulcra SA) (>10)); PEG-60 castor oil (Nikkol CO-60TX (Nikko) (14)); PEG-100 castor oil (Thornley (>10)); PEG-200 castor oil (Eumulgin® PRT 200 (Pulcra SA) (>10)); PEG-5 hydrogenated castor oil (Nikkol HCO-5 (Nikko) (6)); PEG-7 hydrogenated castor oil (Simusol® 989 (Seppic), Cremophor WO7 (BASF) (6)); PEG-10 hydrogenated castor oil (Nikkol HCO-10 (Nikko) (6.5)); PEG-20 hydrogenated castor oil (Nikkol HCO-20 (Nikko) (11)); PEG-25 hydrogenated castor oil (Simusol® 1292 (Seppic), Cerex ELS 250 (Auschem SpA) (11)); PEG-30 hydrogenated castor oil (Nikkol HCO-30 (Nikko) (11)); PEG-40 hydrogenated castor oil (Cremophor RH 40 (BASF), Croduret (Croda), Emulgin HRE 40 (Henkel) (13)); PEG-45 hydrogenated castor oil (Cerex ELS 450 (Auschem Spa) (14)); PEG-50 hydrogenated castor oil (Emalex HC-50 (Nihon Emulsion) (14)); PEG-60 hydrogenated castor oil (Nikkol HCO-60 (Nikko); Cremophor RH 60 (BASF) (15)); PEG-80 hydrogenated castor oil (Nikkol HCO-80 (Nikko) (15)); PEG-100 hydrogenated castor oil (Nikkol HCO-100 (Nikko) (17)); PEG-6 corn oil (Labrafil® M 2125 CS (Gattefosse) (4)); PEG-6 almond oil (Labrafil® M 1966 CS (Gattefosse) (4)); PEG-6 apricot kernel oil (Labrafil® M 1944 CS (Gattefosse) (4)); PEG-6 olive oil (Labrafil® M 1980 CS (Gattefosse) (4)); PEG-6 peanut oil (Labrafil® M 1969 CS (Gattefosse) (4)); PEG-6 hydrogenated palm kernel oil (Labrafil® M 2130 BS (Gattefosse) (4)); PEG-6 palm kernel oil (Labrafil® M 2130 CS (Gattefosse) (4)); PEG-6 triolein (Labrafil® M 2735 CS (Gattefosse) (4)); PEG-8 corn oil (Labrafil® WL 2609 BS (Gattefosse) (6-7)); PEG-20 corn glycerides (Crovol M40 (Croda) (10)); PEG-20 almond glycerides (Crovol A40 (Croda) (10)); PEG-25 trioleate (TAGAT® TO (Goldschmidt) (11)); PEG-40 palm kernel oil (Crovol PK-70 (>10)); PEG-60 corn glycerides (Crovol M70 (Croda) (15)); PEG-60 almond glycerides (Crovol A70 (Croda) (15)); PEG-4 caprylic/capric triglyceride (Labrafac® Hydro (Gattefosse), (4-5)); PEG-8 caprylic/capric glycerides (Labrasol (Gattefosse), Labrafac CM 10 (Gattefosse) (>10)); PEG-6 caprylic/capric glycerides (SOFTIGEN® 767 (Huls), Glycerox 767 (Croda) (19)); Lauroyl macrogol-32 glyceride (GELUCIRE 44/14 (Gattefosse) (14)); Stearoyl macrogol glyceride (GELUCIRE 50/13 (Gattefosse) (13)); Mono, di, tri, tetra esters of vegetable oils and sorbitol (SorbitoGlyceride (Gattefosse) (<10)); Pentaerythrityl tetraisostearate (Crodamol PTIS (Croda) (<10)); Pentaerythrityl distearate (Albunol DS (Taiwan Surf.) (<10)); Pentaerythrityl tetraoleate (Liponate PO-4 (Lipo Chem.) (<10)); Pentaerythrityl tetrastearate (Liponate PS-4 (Lipo Chem.) (<10)); Pentaerythrityl tetracaprylate/tetracaprate (Liponate PE-810 (Lipo Chem.), Crodamol PTC (Croda) (<10)); Pentaerythrityl tetraoctanoate (Nikkol Pentarate 408 (Nikko))); and combinations thereof.

Polyglycolized Fatty Acids: (listed as compound name (common commercial product name (supplier) (HLB)): Polyglyceryl-2 stearate (Nikkol DGMS (Nikko) (5-7)); Polyglyceryl-2 oleate (Nikkol DGMO (Nikko) (5-7)); Polyglyceryl-2 isostearate (Nikkol DGMIS (Nikko) (5-7)); Polyglyceryl-3 oleate (Caprol® 3GO (ABITEC), Drewpol 3-1-O (Stepan) (6.5)); Polyglyceryl-4 oleate (Nikkol Tetraglyn 1-O (Nikko) (5-7)); Polyglyceryl-4 stearate (Nikkol Tetraglyn 1-S (Nikko) (5-6)); Polyglyceryl-6 oleate (Drewpol 6-1-O (Stepan), Nikkol Hexaglyn 1-O (Nikko) (9)); Polyglyceryl-10 laurate (Nikkol Decaglyn 1-L (Nikko) (15)); Polyglyceryl-10 oleate (Nikkol Decaglyn 1-O (Nikko) (14)); Polyglyceryl-10 stearate (Nikkol Decaglyn 1-S (Nikko) (12)); Polyglyceryl-6 ricinoleate (Nikkol Hexaglyn PR-15 (Nikko) (>8)); Polyglyceryl-10 linoleate (Nikkol Decaglyn 1-LN (Nikko) (12)); Polyglyceryl-6 pentaoleate (Nikkol Hexaglyn 5-O (Nikko) (<10)); Polyglyceryl-3 dioleate (Cremophor GO32 (BASF) (<10)); Polyglyceryl-3 distearate (Cremophor GS32 (BASF) (<10)); Polyglyceryl-4 pentaoleate (Nikkol Tetraglyn 5-O (Nikko) (<10)); Polyglyceryl-6 dioleate (Caprol® 6G20 (ABITEC); Hodag PGO-62 (Calgene), PLUROL OLEIQUE CC 497 (Gattefosse) (8.5)); Polyglyceryl-2 dioleate (Nikkol DGDO (Nikko) (7)); Polyglyceryl-10 trioleate (Nikkol Decaglyn 3-O (Nikko) (7)); Polyglyceryl-10 pentaoleate (Nikkol Decaglyn 5-O (Nikko) (3.5)); Polyglyceryl-10 septaoleate (Nikkol Decaglyn 7-O (Nikko) (3)); Polyglyceryl-10 tetraoleate (Caprol® 10G40 (ABITEC); Hodag PGO-62 (CALGENE), Drewpol 10-4-O (Stepan) (6.2)); Polyglyceryl-10 decaisostearate (Nikkol Decaglyn 10-IS (Nikko) (<10)); Polyglyceryl-101 decaoleate (Drewpol 10-10-O (Stepan), Caprol 10G10O (ABITEC), Nikkol Decaglyn 10-O (3.5)); Polyglyceryl-10 mono, dioleate (Caprol® PGE 860 (ABITEC) (11)); Polyglyceryl polyricinoleate (Polymuls (Henkel) (3-20)); and combinations thereof.

Propylene Glycol Fatty Acid Esters: (listed as compound name (common commercial product name (supplier) (HLB)): Propylene glycol monocaprylate (Capryol 90 (Gattefosse), Nikkol Sefsol 218 (Nikko) (<10)); Propylene glycol monolaurate (Lauroglycol 90 (Gattefosse), Lauroglycol FCC (Gattefosse) (<10)); Propylene glycol oleate (Lutrol OP2000 (BASF) (<10)); Propylene glycol myristate (Mirpyl (<10)); Propylene glycol monostearate (ADM PGME-03 (ADM), LIPO PGMS (Lipo Chem.), Aldo® PGHMS (Lonza) (3-4)); Propylene glycol hydroxy stearate (<10)); Propylene glycol ricinoleate (PROPYMULS (Henkel) (<10)); Propylene glycol isostearate (<10)); Propylene glycol monooleate (Myverol P-O6 (Eastman) (<10)); Propylene glycol dicaprylate/dicaprate (Captex® 200 (ABITEC), Miglyol® 840 (Huls), Neobee® M-20 (Stepan) (>6)); Propylene glycol dioctanoate (Captex® 800 (ABITEC) (>6)); Propylene glycol caprylate/caprate (LABRAFAC PG (Gattefosse) (>6)); Propylene glycol dilaurate (>6)); Propylene glycol distearate (Kessco® PGDS (Stepan) (>6)); Propylene glycol dicaprylate (Nikkol Sefsol 228 (Nikko) (>6)); Propylene glycol dicaprate (Nikkol PDD (Nikko) (>6)); and combinations thereof.

Mixtures of Propylene Glycol Esters and Glycerol-Esters: (listed as compound name (common commercial product name (supplier) (HLB)): Oleic (ATMOS 300, ARLACEL 186 (ICI) (3-4)); Stearic (ATMOS 150 (3-4)); and combinations thereof.

Mono- and Diglycerides: (listed as compound name (common commercial product name (supplier) (HLB)): Monopalmitolein (C16:1) (Larodan) (<10)); Monoelaidin (C18:1) (Larodan) (<10)); Monocaproin (C6) (Larodan) (<10)); Monocaprylin (Larodan) (<10)); Monocaprin (Larodan) (<10)); Monolaurin (Larodan) (<10)); Glyceryl monomyristate (C14) (Nikkol MGM (Nikko) (3-4)); Glyceryl monooleate (C18:1) (PECEOL (Gattefosse), Hodag GMO-D, Nikkol MGO (Nikko) (3-4)); Glyceryl monooleate (RYLO series (Danisco), DIMODAN series (Danisco), EMULDAN (Danisco), ALDO® MO FG (Lonza), Kessco GMO (Stepan), MONOMULS® series (Henkel), TEGIN O, DREWMULSE GMO (Stepan), Atlas G-695 (ICI), GMOrphic 80 (Eastman), ADM DMG-40, 70, and 100 (ADM), Myverol (Eastman) (3-4)); Glycerol monooleate/linoleate (OLICINE (Gattefosse)) (3-4)); Glycerol monolinoleate (Maisine (Gattefosse), MYVEROL 18-92, Myverol 18-06 (Eastman) (3-4)); Glyceryl ricinoleate (Softigen® 701 (Huls), HODAG GMR-D (Calgene), ALDO® MR (Lonza) (6)); Glyceryl monolaurate (ALDO® MLD (Lonza), Hodag GML (Calgene) (6.8)); Glycerol monopalmitate (Emalex GMS-P (Nihon) (4)); Glycerol monostearate (Capmul® GMS (ABITEC), Myvaplex (Eastman), IMWITOR® 191 (Huls), CUTINA GMS, Aldo® MS (Lonza), Nikkol MGS series (Nikko) (5-9)); Glyceryl mono-, dioleate (Capmul® GMO-K (ABITEC) (<10)); Glyceryl palmitic/stearic (CUTINA MD-A, ESTAGEL-G18 (<10)); Glyceryl acetate (Lamegin® EE (Grunau GmbH) (<10)); Glyceryl laurate (Imwitor® 312 (Huls), Monomuls® 90-45 (Grunau GmbH), Aldo® MLD (Lonza) (4)); Glyceryl citrate/lactate/oleate/linoleate (Imwitor® 375 (Huls) (<10)); Glyceryl caprylate (Imwitor® 308 (Huls), Capmul® MCMC8 (ABITEC) (5-6)); Glyceryl caprylate/caprate (Capmul® MCM (ABITEC) (5-6)); Caprylic acid mono, diglycerides (Imwitor® 988 (Huls) (5-6)); Caprylic/capric glycerides (Imwitor® 742 (Huls) (<10)); Mono- and diacetylated monoglycerides (Myvacet® 9-45, Myvacet® 9-40, Myvacet® 9-08 (Eastman), Lamegin® (Grunau) (3.8-4)); Glyceryl monostearate (Aldo® MS, Arlacel 129 (ICI), LIPO GMS (Lipo Chem.), Imwitor® 191 (Huls), Myvaplex (Eastman) (4.4)); Lactic acid esters of mono, diglycerides (LAMEGIN GLP (Henkel) (<10)); Dicaproin (C6) (Larodan) (<10); Dicaprin (C10) (Larodan) (<10); Dioctanoin (C8) (Larodan) (<10); Dimyristin (C14) (Larodan) (<10); Dipalmitin (C16) (Larodan) (<10); Distearin (Larodan) (<10); Glyceryl dilaurate (C12) (Capmul® GDL (ABITEC) (3-4)); Glyceryl dioleate (Capmul® GDO (ABITEC) (3-4)); Glycerol esters of fatty acids (GELUCIRE 39/01 (Gattefosse), GELUCIRE 43/01 (Gattefosse) GELUCIRE 37/06 (Gattefosse) (1 6)); Dipalmitolein (C16:1) (Larodan) (<10); 1,2 and 1,3-diolein (C18:1) (Larodan) (<10); Dielaidin (C18:1) (Larodan) (<10); Dilinolein (C18:2) (Larodan) (<10); and combinations thereof.

Sterol and Sterol Derivatives: (listed as compound name (common commercial product name (supplier) (HLB)): Cholesterol, sitosterol, lanosterol (<10)); PEG-24 cholesterol ether (Solulan C-24 (Amerchol) (>10)); PEG-30 cholestanol (Nikkol DHC (Nikko) (>10)); Phytosterol (GENEROL series (Henkel) (<10)); PEG-25 phyto sterol (Nikkol BPSH-25 (Nikko) (>10)); PEG-5 soya sterol (Nikkol BPS-5 (Nikko) (<10)); PEG-10 soya sterol (Nikkol BPS-10 (Nikko) (<10)); PEG-20 soya sterol (Nikkol BPS-20 (Nikko) (<10)); PEG-30 soya sterol (Nikkol BPS-30 (Nikko) (>10)); and combinations thereof.

Polyethylene Glycol Sorbitan Fatty Acid Esters: (listed as compound name (common commercial product name (supplier) (HLB)): PEG-10 sorbitan laurate (Liposorb L-10 (Lipo Chem.) (>10)); PEG-20 sorbitan monolaurate (Tween-20 (Atlas/ICI), Crillet 1 (Croda), DACOL MLS 20 (Condea) (17)); PEG-4 sorbitan monolaurate (Tween-21 (Atlas/ICI), Crillet 11 (Croda) (13)); PEG-80 sorbitan monolaurate (Hodag PSML-80 (Calgene); T-Maz 28 (>10)); PEG-6 sorbitan monolaurate (Nikkol GL-1 (Nikko) (16)); PEG-20 sorbitan monopalmitate (Tween-40 (Atlas/ICI), Crillet 2 (Croda) (16)); PEG-20 sorbitan monostearate (Tween-60 (Atlas/ICI), Crillet 3 (Croda) (15)); PEG-4 sorbitan monostearate (Tween-61 (Atlas/ICI), Crillet 31 (Croda) (9.6)); PEG-8 sorbitan monostearate (DACOL MSS (Condea) (>10)); PEG-6 sorbitan monostearate (Nikkol TS106 (Nikko) (11)); PEG-20 sorbitan tristearate (Tween-65 (Atlas/ICI), Crillet 35 (Croda) (11)); PEG-6 sorbitan tetrastearate (Nikkol GS-6 (Nikko) (3)); PEG-60 sorbitan tetrastearate (Nikkol GS-460 (Nikko) (13)); PEG-5 sorbitan monooleate (Tween-81 (Atlas/ICI), Crillet 41 (Croda) (10)); PEG-6 sorbitan monooleate (Nikkol TO-106 (Nikko) (10)); PEG-20 sorbitan monooleate (Tween-80 (Atlas/ICI), Crillet 4 (Croda) (15)); PEG-40 sorbitan oleate (Emalex ET 8040 (Nihon Emulsion) (18)); PBG-20 sorbitan trioleate (Tween-85 (Atlas/ICI), Crillet 45 (Croda) (11)); PEG-6 sorbitan tetraoleate (Nikkol GO-4 (Nikko) (8.5)); PEG-30 sorbitan tetraoleate (Nikkol GO-430 (Nikko) (12)); PEG-40 sorbitan tetraoleate (Nikkol GO-440 (Nikko) (13)); PEG-20 sorbitan monoisostearate (Tween-120 (Atlas/ICI), Crillet 6 (Croda) (>10)); PEG sorbitol hexaoleate (Atlas G-1086 (ICI) (10)); PEG-6 sorbitol hexastearate (Nikkol GS-6 (Nikko) (3)); and combinations thereof.

Polyethylene Glycol Alkyl Ethers: (listed as compound name (common commercial product name (supplier) (HLB)): PEG-2 oleyl ether,oleth-2 (Brij 92/93 (Atlas/ICI) (4.9)); PEG-3 oleyl ether,oleth-3 (Volpo 3 (Croda) (<10)); PEG-5 oleyl ether,oleth-5 (Volpo 5 (Croda) (<10)); PEG-10 oleyl ether,oleth-10 (Volpo 10 (Croda), Brij 96/97 (Atlas/ICI) (12)); PEG-20 oleyl ether,oleth-20 (Volpo 20 (Croda), Brij 98/99 (Atlas/ICI) (15)); PEG-4 lauryl ether, laureth-4 (Brij 30 (Atlas/ICI) (9.7)); PEG-9 lauryl ether (>10)); PEG-23 lauryl ether, laureth-23 (Brij 35 (Atlas/ICI) (17)); PEG-2 cetyl ether (Brij 52 (ICI) (5.3)); PEG-10 cetyl ether (Brij 56 (ICI) (13)); PEG-20 cetyl ether (BriJ 58 (ICI) (16)); PEG-2 stearyl ether (Brij 72 (ICI) (4.9)); PEG-10 stearyl ether (Brij 76 (ICI) (12)); PEG-20 stearyl ether (Brij 78 (ICI) (15)); PEG-100 stearyl ether (Brij 700 (ICI) (>10)); and combinations thereof.

Sugar Esters: (listed as compound name (common commercial product name (supplier) (HLB)): Sucrose distearate (SUCRO ESTER 7 (Gattefosse), Crodesta F-10 (Croda) (3)); Sucrose distearate/monostearate (SUCRO ESTER 11 (Gattefosse), Crodesta F-110 (Croda) (12)); Sucrose dipalmitate (7.4)); Sucrose monostearate (Crodesta F-160 (Croda) (15)); Sucrose monopalmitate (SUCRO ESTER 15 (Gattefosse) (>10)); Sucrose monolaurate (Saccharose monolaurate 1695 (Mitsubisbi-Kasei) (15)); and combinations thereof.

Polyethylene Glycol Alkyl Phenols: (listed as compound name (common commercial product name (supplier) (HLB)): PEG-10-100 nonyl phenol (Triton X series (Rohm & Haas), Igepal CA series (GAF, USA), Antarox CA series (>10)); (GAF, UK); PEG-15-100 octyl phenol ether (Triton N-series (Rohm & Haas), Igepal CO series (GAF, USA), Antarox CO series (GAF, UK) (>10)); and combinations thereof.

Polyethylene-Polyoxypropylene Block Copolymers (AKA—"poloxamer"): These polymers have the formula: $HO(C_2H_4O)_a(C_3H_6O)_b(C_2H_4O)_aH$ where "a" and "b" denote the number of polyoxyethylene and polyoxypropylene units, respectively. The compounds are listed by generic name, with the corresponding "a" and "b" values. POE-POP Block Copolymers)); (a, b values in)); (HO(C<2>H<4>O)<a>)); (COMPOUND (C<3>H<6>O)<b>(C<2>H<4>O)<a>H (HLB)); (Poloxamer 105 (a=11 (b=16 (8)); (Poloxamer 108 (a=46 (b=16 (>10)); (Poloxamer 122 (a=5 (b=21 (3)); (Poloxamer 123 (a=7 (b=21 (7)); (Poloxamer 124 (a=11 (b=21 (>7)); (Poloxamer 181 (a=3 (b=30)); (Poloxamer 182 (a=8 (b=30 (2)); (Poloxamer 183 (a=10 (b=30)); (Poloxamer 184 (a=13 (b=30)); (Poloxamer 185 (a=19 (b=30)); (Poloxamer 188 (a=75 (b=30 (29)); (Poloxamer 212 (a=8 (b=35)); (Poloxamer 215 (a=24 (b=35)); (Poloxamer 217 (a=52 (b=35)); (Poloxamer 231 (a=16 (b=39)); (Poloxamer 234 (a=22 (b=39)); (Poloxamer 235 (a=27 (b=39)); (Poloxamer 237 (a=62 (b=39 (24)); (Poloxamer 238 (a=97 (b=39)); (Poloxamer 282 (a=10 (b=47)); (Poloxamer 284 (a=21 (b=47)); (Poloxamer 288 (a=122 (b=47 (>10)); (Poloxamer 331 (a=7 (b=54 (0.5)); (Poloxamer 333 (a=20 (b=54)); (Poloxamer 334 (a=31 (b=54)); (Poloxamer 335 (a=38 (b=54)); (Poloxamer 338 (a=128 (b=54)); (Poloxamer 401 (a=6 (b=67)); (Poloxamer 402 (a=13 (b=67)); (Poloxamer 403 (a=21 (b=67)); (Poloxamer 407 (a=98 (b=67)); and combinations thereof.

Sorbitan Fatty Acid Esters: (listed as compound name (common commercial product name (supplier) (HLB)): Sorbitan monolaurate (Span-20 (Atlas/ICI), Crill 1 (Croda), Arlacel 20 (ICI) (8.6)); Sorbitan monopalmitate (Span-40 (Atlas/ICI), Crill 2 (Croda), Nikkol SP-10 (Nikko) (6.7)); Sorbitan monooleate (Span-80 (Atlas/ICI), Crill 4 (Croda), Crill 50 (Croda) (4.3)); Sorbitan monostearate (Span-60 (Atlas/ICI), Crill 3 (Croda), Nikkol SS-10 (Nikko) (4.7)); Sorbitan trioleate (Span-85 (Atlas/ICI), Crill 45 (Croda), Nikkol SO-30 (Nikko) (4.3)); Sorbitan sesquioleate (Arlacel-C (ICI), Crill 43 (Croda), Nikkol SO-15 (Nikko) (3.7)); Sorbitan tristearate (Span-65 (Atlas/ICI) Crill 35 (Croda), Nikkol SS-30 (Nikko) (2.1)); Sorbitan monoisostearate (Crill 6 (Croda), Nikkol SI-10 (Nikko) (4.7)); Sorbitan sesquistearate (Nikkol SS-15 (Nikko) (4.2)); and combinations thereof.

Lower Alcohol Fatty Acid Esters: (listed as compound name (common commercial product name (supplier) (HLB)): Ethyl oleate ((Crodamol EO (Croda), Nikkol EOO (Nikko) (<10)); Isopropyl myristate (Crodamol IPM (Croda) (<10)); Isopropyl palmitate (Crodamol IPP (Croda) (<10)); Ethyl linoleate (Nikkol VF-E (Nikko) (<10)); Isopropyl linoleate (Nikkol VF-IP (Nikko) (<10)); and combinations thereof.

Ionic Surfactants: (listed as compound name (HLB) Fatty acid salts (>10)); Sodium caproate; Sodium caprylate; Sodium caprate; Sodium laurate; Sodium myristate)); Sodium myristolate; Sodium palmitate; Sodium palmitoleate; Sodium oleate (18); Sodium ricinoleate)); Sodium linoleate; Sodium linolenate; Sodium stearate; Sodium lauryl sulfate (40); Sodium tetradecyl sulfate; Sodium lauryl sarcosinate; Sodium dioctyl sulfosuccinate; Bile Salts (>10); Sodium cholate; Sodium taurocholate; Sodium glycocholate; Sodium deoxycholate; Sodium taurodeoxycholate; Sodium glycodeoxycholate; Sodium ursodeoxycholate; Sodium chenodeoxycholate; Sodium taurochenodeoxycholate; Sodium glyco cheno deoxycholate; Sodium cholylsarcosinate; Sodium N-methyl taurocholate; and combinations thereof.

Phospholipids: such as Egg/Soy lecithin (Epikuron™; Ovothin™); Lyso egg/soy lecithin; Hydroxylated lecithin; Lysophosphatidylcholine; Cardiolipin; Sphingomyelin; Phosphatidylcholine; Phosphatidyl ethanolamine; Phosphatidic acid; Phosphatidyl glycerol; Phosphatidyl serine, and combinations thereof.

Phosphoric Acid Esters: Diethanolammonium polyoxyethylene-10 oleyl ether phosphate; Esterification products of fatty alcohols or fatty alcohol ethoxylates with phosphoric acid or anhydride.

Carboxylates, such as: Ether carboxylates (by oxidation of terminal OH group of fatty alcohol ethoxylates) Succinylated monoglycerides; Sodium stearyl fumarate; Stearoyl propylene glycol hydrogen succinate; Mono/diacetylated tartaric acid esters of mono- and diglycerides; Citric acid esters of mono-, diglycerides; Glyceryl-lacto esters of fatty acids; and combinations thereof.

Acyl lactylates such as: lactylic esters of fatty acids; calcium/sodium stearoyl-2-lactylate; calcium/sodium stearoyl lactylate; alginate salts like sodium alginate, calcium alginate and others; and combinations thereof.

Hydrophilic Polymers such as: carboxyvinyl polymer, polyvinylpyrrolidone, polyvinyl alcohol, methacrylic acid copolymers, macrogol, starch, gelatin, dextrin, pullulan, agar, acacia, poly(ethylene glycol), poly(ethylene oxide), poly(vinyl alcohol), poly(ethylene-co-vinyl alcohol), poly(acrylic acid), poly(ethylene-co-acrylic acid), poly(ethyloxazoline), poly(vinyl pyrrolidone), poly(ethylene-co-vinyl pyrrolidone), poly(maleic acid), poly(ethylene-co-maleic acid), poly(acrylamide), or poly(ethylene oxide)-co-poly (propylene oxide); block copolymers, graft copolymers of lactic acid, glycolic acid, epsilon-caprolactone, lactic-co-glycolic acid oligomers, trimethylene carbonate, anhydrides, and amino acids acrylates, benzoquinones, naphthoquinones and the like; N-vinylpyrrolidone-co-vinyl alcohol, poly(ethylene-co-vinyl alcohol); acrylic or methacrylic acid copolymers; carbomers, Chitosan, methacrylates (Eudragits), and combinations thereof.

Acids such as: acetic acid, hydrochloric acid, hydrobromic acid, hydriodic acid, phosphoric acid, sulfuric acid, nitric acid, acrylic acid, adipic acid, alginic acid, alkanesulfonic acid, an amino acid, ascorbic acid, benzoic acid, boric acid, butyric acid, carbonic acid, citric acid, fatty acid, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, salts thereof, and mixtures thereof.

Bases such as: amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrotalcite, magnesium aluminum hydroxide, diisopropylethylamine, ethanolamine, ethylenediamine, triethanolamine, triethylamine, triisopropanolamine, and mixtures of combinations thereof.

Chelating Agents such as: Sodium EDTA, Dieditate Sodium, and mixtures or combinations thereof. Complexing Agents such as: Hydroxypropyl Cyclodextrin, Hydroxy propyl beta Cyclodextrin, sulfabutyl ether cyclodextrin, and mixtures and combinations thereof. Salts such as: salts of acids, bases, salts of fatty acids, fatty acid glycerides, Salts of bile acids, and mixtures and combinations thereof.

Amides such as: for example 2-pyrrolidone, 2-piperidone, .epsilon.-caprolactam, N-alkylpyrrolidone, N-hydroxyalkylpyrrolidone, N-alkylpiperidone, N-alkylcaprolactam, dimethylacetamide, polyvinylpyrrolidone and the like.

Alcohols such as: ethanol, isopropanol, butanol, benzyl alcohol, ethylene glycol, propylene glycol, glycerol, sorbitol, mannitol, dimethyl isosorbide, polyethylene glycol, fatty acid alcohol, vinyl alcohol polypropylene glycol, polyvinyl-alcohol, tocopherols, cellulose cyclodextrins, other derivatives, forms, mixtures thereof, or the like.

Glycerols and Propylene Glycols such as: glycerine, propylene glycol, polypropylene glycol, polypropylene oxides, and mixtures thereof. Polyethylene Glycol (PEG) such as: PEG 300, PEG 400, PEG 4000, PEG 6000, PEG 8000, PEG 20000, and combinations thereof.

Esters such as: ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, epsilon-caprolactone and isomers thereof, .delta.-valerolactone and isomers thereof, beta-butyrolactone and isomers thereof; dimethyl acetamide, dimethyl isosorbide, N-methyl pyrrolidones, monooctanoin, diethylene glycol monoethyl ether, or the like.

Bile acids such as: cholate, taurocholate, glycocholate, deoxycholate, taurodeoxycholate, chenodeoxycholate, glycodeoxycholate, glycochenodeoxycholate, taurochenodeoxycholate, ursodeoxycholate, lithocholate, tauroursodeoxycholate, glycoursodeoxycholate, cholylsarcosine)

Celluloses such as: microcrystalline cellulose, ethyl cellulose (EC), methylethyl cellulose (MEC), carboxymethyl cellulose (CMC), carboxymethyl ethylcellulose (CMEC), hydroxyethyl cellulose (HEC), hydroxypropyl cellulose (HPC), cellulose acetate (CA), cellulose propionate (CPr), cellulose butyrate (CB), cellulose acetate butyrate (CAB), cellulose acetate phthalate (CAP), cellulose acetate trimellitate (CAT), hydroxypropyl methyl cellulose (HPMC), hydroxypropyl methyl cellulose phthalate (HPMCP), hydroxypropyl methyl cellulose acetate succinate (HPMCAS), hydroxypropyl methyl cellulose acetate trimellitate (HPMCAT), and ethylhydroxy ethylcellulose (EHEC), various grades of low viscosity (MW less than or equal to 50,000 daltons) and high viscosity (MW greater than 50,000 daltons) HPMC, and combinations thereof.

Cellulose Esters such as: Cellulose acetate, Cellulose Acetate Butyrate, Cellulose acetate phthalate, Hydroxypropyl methylcellulose phthalate, and combinations thereof.

Mucoadhesive Polymers such as for example tocopherols such as for example tocopherol, tocopherol acetate, tocopherol succinate, and combinations thereof.

Amino Acids and Modified Amino acids such as: aminoboronic acid derivatives, n-acetylcysteine, and mixtures thereof.

Sugars such as: maltose, sucrose, dextrose, lactose, fructose, mannitol, sucralose, fructalose, trehelose, dextrose, maltodextrose, and combinations thereof.

Sugar Alcohols such as: mannitol, xylitol, sorbitol, combinations thereof, and the like Osmotic agents such as: Hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP) and crosslinked PVP, polyvinyl alcohol (PVA), PVA/PVP copolymers and PVA/PVP copolymers with hydrophobic monomers such as methyl methacrylate, vinyl acetate, and the like, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carbox cellulose (CEC), sodium alginate, polycarbophil, gelatin, xanthan gum, and sodium starch glycolate and the like.

Other carriers such as: dibasic calcium phosphate, croscarmellose sodium, sodium starch glycolate, sodium alginate, phospholipids, lecithins, proteins (e.g., collagen, gelatin, Zein, gluten, mussel protein, lipoprotein); carbohydrates (e.g., alginates, carrageenan, cellulose derivatives, pectin, starch); gums (e.g., xanthan gum, gum Arabic, gum tragacanth, gum acacia); spermaceti; natural or synthetic waxes; carnuaba wax; fatty acids (e.g., stearic acid, hydroxystearic acid); Magnesium stearate, calcium stearate, titanium dioxide, polyacrylic acid, silicates, magnesium aluminum silicates, siloxanes, mimeticones, paraffins, fatty alcohols; dibutyl phthalate; dibutyl sebacate; diethyl phthalate; dimethyl phthalate; triethyl citrate; butyl and glycol esters of fatty acids; mineral oil; cetyl alcohol; stearyl alcohol; camphor oil; triethyl citrate, shellacs, benzalkonium chloride, methyl paraben, propyl paraben, sodium benzoate and the like.

In one embodiment, the pharmaceutical composition or oral dosage form can be formulated to include at least one of the following preferred carriers: citric acid, maleic acid, tartaric acid, ascorbic acid, lactic acid, and salts thereof, potassium hydroxide, sodium hydroxide, sodium hydrogen carbonate, calcium carbonate, silicon dioxide, magnesium aluminum silicate, triethylamine, fatty acid glycerides, pyrrolidone, polyvinylpyrrolidone, ethyl alcohol, benzyl alcohol, glycerol, propylene glycol, polyethylene glycol, triethylcitrate, triacetin, benzyl benzoate, bile acid, salts of bile acid, ethyl cellulose, hydroxypropyl ethyl cellulose, cellulose esters, carbomer, methacrylates, polyvinyl alcohol, gelatin, distearin, monopalmitolein tocopherol, tocopherol succinate, corn oil, olive oil, peanut oil, safflower oil, sesame oil, soybean oil, hydrogenated castor oil, glyceryl tricaprate, glyceryl trilinoleate, glyceryl tricaprylate/caprate, glyceryl tricaprylate/caprate/linoleate, saturated polyglycolized glycerides, linoleic glycerides, caprylic/capric glycerides, capric acid, caprylic acid, palmitic acid, Lauric acid, stearic acid, linoleic acid, oleic acid, arachidonic acid, eicosapentaenoic acid, docosahexaenoic acid, glyceryl monooleate, glyceryl monolinoleate, glyceryl monolaurate, glycerol monostearate, glyceryl distearate, glyceryl palmitostearate, glyceryl laurate, glyceryl caprylate, PEG-6 corn oil, PEG-6 apricot kernel oil, stearoyl macrogol glyceride, PEG-20 sorbitan monostearate, PEG-40 hydrogenated castor oil, PEG-35 castor oil, sodium oleate, sodium lauryl sulfate, sodium lauryl sarcosinate, sodium dioctyl sulfosuccinate, polyglyceryl-3 oleate, polyglyceryl-10 oleate, polyglyceryl-6 dioleate, polyglyceryl-10 mono, dioleate, poloxamer 188, poloxamer 108, poloxamer 182, propylene glycol monocaprylate, propylene glycol monolaurate, propylene glycol dicaprylate/dicaprate, propylene glycol caprylate/caprate, sorbitan monolaurate, sorbitan monopalmitate, sorbitan monooleate, sorbitan monostearate, sorbitan sesquioleate, sorbitan sesquistearate, maltose, sucrose, fructose, mannitol, xylitol, and combinations thereof.

In one embodiment, the pharmaceutical compositions or oral dosage forms of the present invention can be formulated to include a hydrophilic additive. In another embodiment, the hydrophilic additive can be a hydrophilic surfactant. In one embodiment, when the hydrophilic additive includes a hydrophilic surfactants, the hydrophilic surfactant does not appreciably solubilize the ester of 17-hydroxyprogesterone. Non-limiting examples of hydrophilic additives include salts of citric acid, maleic acid, tartaric acid, acetic acid, ascorbic acid, benzoic acid and lactic acid, potassium hydroxide, sodium hydroxide, sodium hydrogen carbonate, calcium carbonate, silicon dioxide, magnesium aluminum silicate, hydroxypropyl cyclodextrin, fatty acid glycerides, salts of bile acids, pyrrolidone, polyvinylpyrrolidone, ethyl alcohol, benzyl alcohol, glycerol, propylene glycol, polyethylene glycol methyl cellulose, hydroxypropyl methyl cellulose, cellulose ssters, carbomer, chitosan, methacrylates, polyvinyl alcohol, gelatin, PEG-8 caprylic/capric glycerides, lauroyl macrogol-32 glyceride, stearoyl macrogol glyceride, PEG-40 hydrogenated castor oil, PEG-35 castor oil, sodium oleate, sodium lauryl sulfate, sodium lauryl sarcosinate, sodium dioctyl sulfosuccinate, PEG-10 laurate, PEG-20 oleate, PEG-30 stearate, PEG-40 laurate, PEG-20 glyceryl laurate, PEG-20 glyceryl tearate, PEG-40 glyceryl laurate, PEG-20 glyceryl oleate, PEG-10 sorbitan laurate, PEG-20 sorbitan monolaurate, PEG-20 sorbitan monooleate, polyglyceryl-10 oleate, polyglyceryl-10 mono, dioleate, poloxamer 188, poloxamer 108, maltose, sucrose, fructose, mannitol, xylitol, and combinations thereof.

In another particular embodiment, the carrier can be a hydrophilic surfactant and can be ionic or non-ionic surfactant. Non-limiting examples of hydrophilic surfactants include proteins, gelatin, salts of bile acids, PEG-8 caprylic/capric glycerides, lauroyl macrogol-32 glyceride, stearoyl macrogol glyceride, PEG-40 hydrogenated castor oil, PEG-35 castor oil, sodium oleate, sodium lauryl sulfate, sodium lauryl sarcosinate, sodium dioctyl sulfosuccinate, PEG-10 laurate, PEG-20 oleate, PEG-30 stearate, PEG-40 laurate, PEG-20 glyceryl laurate, PEG-20 glyceryl tearate, PEG-40 glyceryl laurate, PEG-20 glyceryl oleate, PEG-10 sorbitan laurate, PEG-20 sorbitan monolaurate, PEG-20 sorbitan monooleate, polyglyceryl-10 oleate, polyglyceryl-10 mono, dioleate, poloxamer 188, poloxamer 108, and combinations thereof.

In one embodiment, the hydrophilic additive can be free of hydrophilic surfactants, and can be citric acid, maleic acid, tartaric acid, acetic acid, ascorbic acid, benzoic acid, lactic acid, potassium hydroxide, sodium hydroxide, sodium hydrogen carbonate, calcium carbonate, silicon dioxide, magnesium aluminum silicate, hydroxypropyl cyclodextrin, pyrrolidone, polyvinylpyrrolidone, ethyl alcohol, benzyl alcohol, glycerol, propylene glycol, polyethylene glycol, methyl cellulose, hydroxypropyl methyl cellulose, cellulose esters, carbomer, chitosan, methacrylates, polyvinyl alcohol, gelatin, maltose, sucrose, fructose, mannitol, xylitol, and combinations thereof.

In another embodiment, the carrier of the pharmaceutical compositions or oral dosage forms can include a lipophilic additive. Non-limiting examples of lipophilic additives include tributylcitrate, triethylcitrate, triacetin, ethyl cellulose, cellulose esters, cellulose acetate, cellulose acetates butyrate, cellulose acetate phthalate, hydroxypropyl methylcellulose phthalate, tocopherol, tocopherol acetate, tocopherol succinate, corn oil, olive oil, peanut oil, safflower oil, sesame oil, soybean oil, hydrogenated castor oil, glyceryl tricaprate, glyceryl trilaurate, glyceryl trioleate, glyceryl trilinoleate, glyceryl tricaprylate/caprate, glyceryl tricaprylate/caprate/laurate, glyceryl tricaprylate/caprate/linoleate, glyceryl tricaprylate/caprate/stearate, saturated polyglycolized glycerides linoleic glycerides, caprylic/capric glycerides capric acid, caprylic acid, palmitic acid, lauric acid, stearic acid, linoleic acid, oleic acid, arachidonic acid, eicosapentaenoic acid, docosahexaenoic acid, glyceryl monooleate, glyceryl monolinoleate, glyceryl monolaurate, glycerol monostearate, glyceryl distearate, glyceryl palmitostearate, glyceryl laurate, glyceryl caprylate, distearin, monopalmitolein, monolaurin, ethyl oleate, PEG-6 corn oil, PEG-6 apricot kernel oil, PEG-4 caprylic/capric triglyceride, PEG-20 sorbitan monostearate, PEG-4 laurate, PEG-6 dilaurate, polyglyceryl-3 oleate, polyglyceryl-6 dioleate, poloxamer 182, propylene glycol monocaprylate, propylene glycol monolaurate, propylene glycol dicaprylate/dicaprate, propylene glycol caprylate/caprate, sorbitan monolaurate, sorbitan monopalmitate, sorbitan monooleate, sorbitan monostearate, sorbitan sesquioleate, sorbitan sesquistearate, and combinations thereof. In one embodiment, the carrier of the current invention can include at least 50 wt % of lipophilic additive.

In a particular embodiment, the lipophilic additive is at least one agent selected from tributylcitrate, triethylcitrate, triacetin, ethyl cellulose, cellulose esters, cellulose acetate, cellulose acetates butyrate, cellulose acetate phthalate, hydroxypropyl methylcellulose phthalate, tocopherol, tocopherol acetate, tocopherol succinate, triglycerides, corn oil, olive oil, peanut oil, safflower oil, sesame oil, soybean oil, hydrogenated castor oil, glyceryl tricaprate, glyceryl trilaurate, glyceryl trioleate, glyceryl trilinoleate, glyceryl tricaprylate/caprate, glyceryl tricaprylate/caprate/laurate, glyceryl tricaprylate/caprate/linoleate, glyceryl tricaprylate/caprate/stearate, saturated polyglycolized glycerides linoleic glycerides, caprylic/capric glycerides, capric acid, caprylic acid, palmitic acid, lauric acid, stearic acid, linoleic acid, oleic acid, arachidonic acid, eicosapentaenoic acid, docosahexaenoic acid, glyceryl distearate, glyceryl palmitostearate, distearin, tristearin, paraffin oil, bess wax, animal fat, phytosterol, cholesterol, shellac and combinations thereof.

In a particular embodiment, the lipophilic additive is a triglyceride. Non-limiting examples of triglycerides suitable for this invention include corn oil, olive oil, peanut oil, palm oil, coconut oil, arachis oil, safflower oil, sesame oil, soybean oil, castor oil, primrose oil, cotton seed oil, vegetable oil, borage oil, linseed oil, flax seed oil, omega oils, partially or fully hydrogenated castor oil, fish oil, shark oil, whale oil, seal oil, glyceryl tricaprate, glyceryl trilaurate, glyceryl trioleate, glyceryl trilinoleate, glyceryl tricaprylate/caprate, glyceryl tricaprylate/caprate/laurate, glyceryl tricaprylate/caprate/linoleate, glyceryl tricaprylate/caprate/stearate, saturated polyglycolized glycerides linoleic glycerides, caprylic/capric glycerides, tristearin and the like, and combinations thereof.

In one embodiment, the lipophilic additive can be free of lipophilic surfactants. In one particular embodiment, the carrier is a lipophilic surfactant. Non-limiting examples of lipophilic surfactants suitable for this invention include tributylcitrate, triethylcitrate, triacetin, ethyl cellulose, cellulose esters, cellulose acetate, cellulose acetates butyrate, benzyl benzoate, cellulose acetate phthalate, hydroxypropyl methylcellulose phthalate, tocopherol, tocopherol acetate, tocopherol succinate, corn oil, olive oil, peanut oil, safflower oil, sesame oil, soybean oil, hydrogenated castor oil, glyceryl tricaprate, glyceryl trilaurate, glyceryl trioleate, glyceryl trilinoleate, glyceryl tricaprylate/caprate, glyceryl tricaprylate/caprate/laurate, glyceryl tricaprylate/caprate/linoleate, glyceryl tricaprylate/caprate/stearate, saturated polyglycolized glycerides linoleic glycerides, caprylic/capric glycerides capric acid, caprylic acid, palmitic acid, lauric acid, stearic acid, linoleic acid, oleic acid, arachidonic acid, eicosapentaenoic acid, docosahexaenoic acid, glyceryl monooleate, glyceryl monolinoleate, glyceryl monolaurate, glycerol monostearate, glyceryl distearate, glyceryl palmitostearate, glyceryl laurate, glyceryl caprylate, distearin, monopalmitolein, monolaurin, ethyl oleate, PEG-6 corn oil, PEG-6 apricot kernel oil, PEG-4 caprylic/capric triglyceride, PEG-20 sorbitan monostearate, PEG-4 laurate, PEG-6 dilaurate, polyglyceryl-3 oleate, polyglyceryl-6 dioleate, poloxamer 182, propylene glycol monocaprylate, propylene glycol monolaurate, propylene glycol dicaprylate/dicaprate, propylene glycol caprylate/caprate, sorbitan monolaurate, sorbitan monopalmitate, sorbitan monooleate, sorbitan monostearate, sorbitan sesquioleate, sorbitan sesquistearate, and combinations thereof.

In another particular embodiment, the compositions or dosage form of the present invention can be free of triglycerides, or substantially free of triglycerides. Thus, in one embodiment, the present invention does not include lipophilic or hydrophilic additive which contain triglycerides as an intended or added component. However, it should be appreciated that the present invention does not exclude the use of lipophilic or hydrophilic additives which contain small amounts of triglycerides as impurities or as unreacted starting material. It is expected that when such lipophilic or hydrophilic additive is used in the compositions of the present invention, the total triglyceride content does not exceed 5% by weight of the composition or dosage form. Thus, "substantially triglyceride-free" should be understood as meaning free of added triglycerides, and the triglyceride impurity from the lipophilic or hydrophilic additives constitute about 5%, or less than 5%, less than 2%, or preferably 0% (triglyceride free), by weight of the composition. Further, the present invention does not exclude lipophilic or hydrophilic additives that are derivatives of triglycerides, such as for example polyethylene glycol or propylene glycol derivatives of triglycerides; while these derivatized triglycerides may have surfactant properties, the triglycerides are not surfactants by themselves.

Non-limiting examples of such lipophilic additives include tributylcitrate, triethylcitrate, triacetin, ethyl cellulose, cellulose esters, cellulose acetate, cellulose acetates butyrate, cellulose acetate phthalate, hydroxypropyl methylcellulose phthalate, tocopherol, tocopherol acetate, tocopherol succinate, saturated polyglycolized glycerides linoleic glycerides, caprylic/capric glycerides capric acid, caprylic acid, palmitic acid, lauric acid, stearic acid, linoleic acid, oleic acid, arachidonic acid, eicosapentaenoic acid, benzyl benzoate, docosahexaenoic acid, glyceryl monooleate, glyceryl monolinoleate, glyceryl monolaurate, glycerol monostearate, glyceryl distearate, glyceryl palmitostearate, glyceryl laurate, glyceryl caprylate, distearin, monopalmitolein, monolaurin, ethyl oleate, PEG-6 corn oil, PEG-6 apricot kernel oil, PEG-4 caprylic/capric triglyceride, PEG-20 sorbitan monostearate, PEG-4 laurate, PEG-6 dilaurate, polyglyceryl-3 oleate, polyglyceryl-6 dioleate, poloxamer 182, propylene glycol monocaprylate, propylene glycol monolaurate, propylene glycol dicaprylate/dicaprate, propylene glycol caprylate/caprate, sorbitan monolaurate, sorbitan monopalmitate, sorbitan monooleate, sorbitan monostearate, sorbitan sesquioleate, sorbitan sesquistearate, and combinations thereof.

In some embodiments, the carrier of the current invention can be a control release agent. In a particular embodiment, the control release agent is selected from the group consisting of the said hydrophilic additives or lipophilic additives or a mixture thereof. In another particular embodiment, the compositions or dosage forms of the present invention can be free of lipophilic surfactant. In another particular embodiment, the compositions or dosage form of the present invention can be free of lipophilic additive.

As discussed above, in some embodiments, the pharmaceutical compositions and the oral dosage forms of the present disclosure can include at least one hydrophilic additive and at least one lipophilic additive. In one embodiment, when both a hydrophilic additive and a lipophilic additive are present, they can be present at a lipophilic additive to hydrophilic additive ratio of about 99:1 to about 1:99. In one embodiment, the lipophilic additive to hydrophilic additive ratio can be about 95:5 to about 5:95. In another embodiment, the lipophilic additive to hydrophilic additive ratio can be about 90:10 to about 10:90. In one embodiment, the lipophilic additive to hydrophilic additive ratio can be of about 90:10 to about 1:99. In another specific embodiment, the lipophilic additive to hydrophilic additive ratio can be of about 80:20 to about 20:80. In another specific embodiment, the lipophilic additive to hydrophilic additive ratio can be of about 70:30 to about 30:70. In another specific embodiment, the lipophilic additive to hydrophilic additive ratio can be of about 60:40 to about 40:60. In another specific embodiment, the lipophilic additive to hydrophilic additive ratio can be about 50:50.

In a separate embodiment, when both a hydrophilic surfactant and a lipophilic additive are present, they can be present in amounts such that when 1 part by weight of the mixture of the hydrophilic surfactant and lipophilic additive is mixed 99 parts of an aqueous diluent, the dispersion so obtained so obtained can be colloidal, hazy or unclear. For example, the aqueous diluent used for dispersion is either water or 0.5% w/v sodium lauryl sulfate in water. In a specific embodiment, the dispersion can exhibit an absorbance greater than 0.1 when determined using a spectrophotometer at 400 nm. In another specific embodiment, the absorbance is greater than 0.3 at 400 nm. In another embodiment, the mean particle size of the dispersion is about 60 nm or more. In another specific embodiment, the mean particle size of the dispersion is about 100 nm or more. In another specific embodiment, the mean particle size of the dispersion is about 150 nm or more. In yet another specific embodiment, the mean particle size of the dispersion is about 200 nm or more. In yet another specific embodiment, the mean particle size of the dispersion is about 250 nm or more. For example, the aqueous diluent used for dispersion is either water or 0.5% w/v sodium lauryl sulfate in water. For the purpose of this invention, the dispersion is deemed clear if it appears clear to the naked eye. In one embodiment, the dispersion can be clear.

The carrier can be present in an amount sufficient to solubilize the ester of 17 hydroxyprogesterone. In some aspects, the carrier of the present invention aids in solubilizing a significant amount of the ester of 17-hydroxyprogesterone in the composition. In one embodiment, the carrier can solubilize 20 wt % or more of the amount of the ester of 17-hydrxoyprogesterone. In another embodiment, the carrier can aid loading of greater than about 10% w/w/ of the ester in the composition and/or dosage form. In another embodiment, the loading achieved by the carrier can be greater than about 12% w/w of the composition and/or dosage form. In another embodiment, the loading achieved by the carrier can be greater than about 15% w/w of the composition and/or dosage form. In another embodiment, the loading attained by inclusion of the carrier can be greater than about 18% w/w of the composition and/or dosage form. In further embodiments, the loading attained by inclusion of the carrier can be greater than about 20%; greater than about 25%, greater than about 30%, greater than about 35%, greater than about 40%, greater than about 50%, greater than about 60%, greater than about 75%, or greater than about 90%, with each percentage based on w/w of the composition and/or dosage form.

In one embodiment, the carrier can include benzyl alcohol, benzyl benzoate, mixtures thereof. In another embodiment, the carrier can include benzyl alcohol, benzyl benzoate, or mixtures thereof and the amount of the ester of 17-hydroxyprogesterone can be between about 5 to about 80% w/w of the total composition. In one embodiment, when the carrier includes benzyl alcohol, benzyl benzoate, or mixtures thereof, the amount of the ester of 17-hydroxyprogesterone can be between about 5 to about 80% w/w of the total composition. In one embodiment, the amount of the ester of 17 hydroxyprogesterone can be between 5% to about 60% w/w of the total composition. In another specific embodiment, when the carrier includes benzyl alcohol, benzyl benzoate, or mixtures thereof, the amount of the ester of 17-hydroxyprogesterone can be between about 5 to about 40% w/w of the total composition. In another specific embodiment, when the carrier includes benzyl alcohol, benzyl benzoate, or mixtures thereof, the amount of the ester of 17-hydroxyprogesterone can be between about 5 to about 30% w/w of the total composition. In another specific embodiment, when the carrier includes benzyl alcohol, benzyl benzoate, or mixtures thereof, the amount of the ester of 17-hydroxyprogesterone can be between about 5 to about 25% w/w of the total composition. In one specific embodiment, when the carrier includes benzyl alcohol, benzyl benzoate, or mixtures thereof, the ester of 17-hydroxyprogesterone can be fully solubilized in the composition and/or the dosage form. In another specific embodiment, the ester of 17-hydroxyprogesterone can be partially solubilized in the dosage form. In another specific embodiment, the ester of 17-hydroxyprogesterone can be 17-hydroxyprogesterone caproate.

In one embodiment the ratio of the amount of the ester of 17-hydroxyprogesterone to the sum of the amounts of benzyl alcohol and benzyl benzoate present in the composition or oral dosage form can be about 1:0.01 (W/W) to about 1:5 (W/W). In another embodiment, the ratio can be about 1:0.01 (W/W) to about 1:3.5 (W/W). In another embodiment, the ratio of the amount of the ester of 17-hydroxyprogesterone to the sum of the amounts of benzyl alcohol and benzyl benzoate present in the composition or oral dosage form can be about 1:0.01 (W/W) to about 1:2.5 (W/W). In another embodiment, the ratio of the amount of the ester of 17-hydroxyprogesterone to the sum of the amounts of benzyl alcohol and benzyl benzoate present in the composition or oral dosage form can be about 1:0.01 to about 1:2 (W/W).

The pharmaceutical compositions and oral dosage forms can be formulated and delivered in a variety of solid or liquid dosage forms. Non-limiting examples of such dosage forms include powder, granulate, particulate, bead, pellet, sprinkle, suspension, solution, tablet, capsule, and combinations thereof. In one embodiment, the pharmaceutical composition or oral dosage form can be in the form of a capsule. In another embodiment, the pharmaceutical composition or oral dosage form can be in the form of a tablet. In one embodiment, the dosage form is a hard or a soft capsule. The capsule can be made of conventional capsule shell materials known in the art; such materials can include, but are not limited to gelatins, celluloses, starches, methacrylates, carrageenans, polyvinyl alcohols, and the like. In another embodiment, the capsule is an immediate release dosage form. In yet another embodiment, the capsule is a controlled release dosage form. In another embodiment, the tablet is an immediate release dosage form. In another embodiment, the tablet is a controlled release dosage form.

In one embodiment, the volume of the capsule can be about 1.5 mL or less. In another embodiment, the volume of capsule can be about 1.2 mL or less. In one particular embodiment, the volume of the capsule can be about 0.8 mL or less. In another embodiment, the ratio of the weight of fill material encapsulated within the capsule to the capsule volume can be between about 0.3 g/mL to about 3.5 g/mL. In a particular embodiment, the ratio can be between 0.6 g/mL to about 2.5 g/mL. In another particular embodiment, the ratio can be between 0.6 g/mL to about 1.2 g/mL.

In another embodiment, the pharmaceutical capsule oral dosage form of the current invention can have a ratio of the amount of the ester of 17-hydroxyprogesterone in the composition to the fill volume of the capsule between about 0.02 g/mL to about 0.8 g/mL. In another embodiment, the ratio can be between about 0.02 g/mL to about 0.7 g/mL. In a specific embodiment, the ratio can be between about 0.02 g/mL to about 0.5 g/mL. In another specific embodiment, the ratio can be between about 0.05 g/mL to about 0.5 g/mL. In another specific embodiment, the ratio can be between about 0.05 g/mL to about 0.35 g/mL. In another specific embodiment, the ratio can be between about 0.05 g/mL to about 0.3 g/mL. In another specific embodiment, the ratio can be between about 0.1 g/mL to about 0.25 g/mL.

The oral dosage forms of the present invention can be formulated to include an amount of an ester of 17-hydroxyprogesterone equivalent to about 10 mg to about 800 mg of 17-hydroxyprogesterone. In one embodiment, the oral dosage form can be formulated to include an amount of ester of 17-hydroxyprogesterone equivalent to 20 mg to about 400 mg of 17-hydroxyprogesterone. The pharmaceutical composition and oral dosage forms of the present invention can be formulated to be administered to a subject in order to provide a daily dose of the ester of 17-hydroxyprogesterone that is equivalent to about 40 mg to about 3200 mg of 17-hydroxyprogesterone. In one embodiment, the oral dosage form can be a capsule and the capsule includes from about 10 mg to about 300 mg 17-hydroxyprogesterone caproate. In another embodiment, the oral dosage form can be a tablet and the tablet includes from about 20 mg to about 800 mg of 17-hydroxyprogesterone caproate.

In order to provide a desired daily dose, the pharmaceutical compositions and oral dosage forms can be formulated to be administered at various dosing intervals. In one embodiment, the compositions or oral dosage forms can be formulated for administration about once every 8 hours. In another embodiment, the compositions or oral dosage forms can be formulated for administration to a subject, such as a human subject, once every 6 hours. In another embodiment, the compositions or oral dosage forms can be formulated for administration about once every 12 hours. In yet a further embodiment, the compositions or oral dosage forms can be formulated for administration about once every 24 hours.

In one aspect, the oral dosage forms of the present invention can be used to treat pregnant female subjects who are at risk of preterm birth. The methods of treatment include the step of orally administering to the female subject the oral pharmaceutical composition. In another embodiment, the oral dosage forms can be administered to subjects in need thereof. The administration of the oral dosage form can treat at least one condition selected from preterm labor, preterm birth, infertility and miscarriage. In one embodiment, the subject receiving administration of the pharmaceutical composition or oral dosage form can be experiencing or be at risk of at least two of: singleton pregnancy, history of preterm labor and/or preterm birth, history of preterm delivery, shortened cervix, and effaced cervix, history of more at least one miscarriage, and history of multifetal gestation. The conditions and the relative treatment can be based on their primary and secondary outcome measurements associated with the administration of the ester of 17-hydroxyprogesterone.

In one embodiment, upon single administration to a human subject, the pharmaceutical compositions or oral dosage forms of the present invention comprising an ester of 17-hydroxyprogesterone can provide a 17-hydroxyprogesterone equivalent $C_{avg\text{-}24\,h}$ greater than about 0.7 ng/mL. In another embodiment, the oral dosage form or the composition can provide a $C_{avg\text{-}24\,h}$ of 17-hydroxyprogesterone equivalents greater than about 10 ng/mL. In another embodiment, the oral dosage form or the composition can provide a $C_{avg\text{-}24\,h}$ of 17-hydroxyprogesterone equivalents greater than about 30 ng/mL. In another embodiment, the oral dosage form or the composition can provide a $C_{avg\text{-}24\,h}$ of 17-hydroxyprogesterone equivalents greater than about 50 ng/mL. In yet a further embodiment, the oral dosage form or the composition can provide a $C_{avg\text{-}24\,h}$ of 17-hydroxyprogesterone equivalents greater than about 100 ng/mL. In one embodiment, the said 17-hydroxyprogesterone equivalent $C_{avg\text{-}24\,h}$ is determined by an HPLC-MS/MS method of analysis of the plasma, serum or blood samples collected following the oral administration.

In one embodiment, upon single administration to a human subject the pharmaceutical compositions or oral dosage forms of the present invention comprising 17-hydroxyprogesterone caproate, can provide a 17-hydroxyprogesterone caproate $C_{avg\text{-}24\,h}$ equal to about 1.0 ng/mL or more. In another embodiment, the oral dosage form or the composition can provide a 17-hydroxyprogesterone caproate $C_{avg\text{-}24\,h}$ equal to about 20 ng/mL or more. In another embodiment, the oral dosage form or the composition can provide a 17-hydroxyprogesterone caproate $C_{avg\text{-}24\,h}$ equal to about 50 ng/mL or more. In another embodiment, the oral dosage form or the composition can provide a 17-hydroxyprogesterone caproate $C_{avg\text{-}24\,h}$ equal to about 100 ng/mL or more. In one embodiment, the said 17-hydroxyprogesterone caproate $C_{avg\text{-}24\,h}$ is determined by an HPLC-MS/MS method of analysis of the plasma, serum or blood samples collected following the oral administration.

It was surprisingly found that the compositions and/or dosage forms of this invention provided significantly enhanced bioavailability of 17 hydroxyprogesterone caproate as a function of the oral dose of the 17 hydroxyprogesterone caproate administered to a subject. Accordingly, the compositions or dosage forms of this invention provide, upon single dose oral administration, an $AUC_{(0\text{-}24\,h)}$ to dose ratio of about 10 or less, wherein the dose is the amount in mg of the 17-hydroxyprogesterone caproate administered. In one embodiment, the ratio of the 17-hydroxyprogesterone caproate $AUC_{(0\text{-}24\,h)}$ to dose of the 17-hydroxyprogesterone caproate administered can be about 0.2 ng*h mL$^{-1}$ mg$^{-1}$ to about 10 ng*h mL$^{-1}$ mg$^{-1}$. In another embodiment, the ratio of the 17-hydroxyprogesterone caproate $AUC_{(0\text{-}24\,h)}$ to dose of the 17-hydroxyprogesterone caproate administered can be about 0.3 ng*h mL$^{-1}$ mg$^{-1}$ to about 7 ng*h mL$^{-1}$ mg$^{-1}$. In a specific embodiment, the $AUC_{(0\text{-}24\,h)}$ to dose ratio is between about 0.5 and about 6 ng*h mL$^{-1}$ mg$^{-1}$.

In a specific embodiment, upon single administration of the pharmaceutical compositions or oral dosage forms containing 17-hydroxyprogesterone caproate of the present invention to a human subject under fed condition, the oral dosage form or pharmaceutical composition can provide a 17-hydroxyprogesterone caproate $C_{avg\text{-}24\,h}$ of greater than about 1.0 ng/mL. In another specific embodiment, the pharmaceutical compositions or oral dosage forms containing 17-hydroxyprogesterone of the present invention can provide a steady state 17-hydroxyprogesterone caproate $C_{avg\text{-}24\,h}$ of greater than about 1.0 ng/mL, when administered to a human subject under fed condition. In one embodiment, the said $C_{avg\text{-}24\,h}$ is determined by an HPLC-MS/MS method of analysis of the plasma, serum or blood samples collected following the administration. In another embodiment, the compositions and oral dosage forms disclosed herein can be orally administered with food or without regards to the food or food content. In a specific embodiment, the compositions and oral dosage forms containing caproate ester of 17-hydroxyprogesterone as disclosed herein can be orally administered with food or without regards to the food or food content.

In one embodiment, the oral dosage form can be orally administered with food or under fed condition. In another embodiment, the composition or oral dosage form can be administered with a normal or standard meal. In a specific embodiment, the composition or oral dosage form can be administered with a food or meal, such as a meal that provides about 200 calories to about 1000 calories of energy. In another specific embodiment, the composition or oral dosage form can be administered with a meal that provides about 50% of the calories from the fat. In another embodiment, the composition or oral dosage form can be administered with a high-fat, high calorie meal. In another embodiment, the composition or oral dosage form can be administered with a standard meal that provides about 500 calories to about 1000 calories of energy. The compositional make-up of the meals that are administered can vary depending on the tastes and dietary needs of a subject. However, in some situations it may be beneficial to administer the compositions and oral dosage forms with meals that provide no fat to about 50 g of fat. In one embodiment, the meal can provide about 3 g to about 50 g of fat. In yet a further embodiment, the meal can provide 10 g to about 50 g of fat. In yet another embodiment, the meal can provide about 15 g to about 35 g of fat. In one embodiment, when the oral dosage form is administered to a human female, it can be done without regard to the presence of or nutritional make-up of a meal. In another embodiment, when administering the oral dosage form, the total daily dose of the ester of 17 HP administered to human female subject with food or under fed condition is from about 20% to about 80% of the total daily dose administered without meals, for a similar therapeutic benefit. In a specific embodiment, the daily dose under fed condition is from about 20% to about 60% of the total daily dose administered without meals, for a similar therapeutic benefit. In another embodiment, the composition or oral dosage form can be administered without food or under fasted condition.

The oral bioavailability of the ester of 17-hydroxyprogesterone can be enhanced by using the said ester in the form of fine particulate, for example milled, micronized or nano-sized etc, in the composition and/or the dosage form of the current invention. Further, the oral bioavailability can be enhanced by using the ester along with a carrier that aids the release of at least 20% more of the ester from the composition or dosage form when exposed to an aqueous medium compared to an equivalent dose of the ester without the carrier of the current invention. In a specific embodiment the oral bioavailability of the caproate ester of 17-hydroxyprogesterone can be enhanced by using the said ester in the form of fine particulate, for example milled, micronized or nano-sized or combinations thereof in the composition and/or the dosage form of the current invention.

Accordingly, in one embodiment, the oral bioavailability of the ester of 17-hydroxyprogesterone is at least 10% more for the compositions or a dosage forms of the current invention that releases at least 20% of the ester in an aqueous medium compared to an equivalent dose of the ester present in an "untreated" particulate form such as for example as unmilled or unmicronized particulate forms. In another embodiment, the oral bioavailability of the ester of 17-hydroxyprogesterone is at least 10% more for the compositions or a dosage forms of the current invention that releases at least 20% more of the ester from the composition or dosage form when exposed to an aqueous medium compared to an equivalent dose of the ester without the carrier of the current invention. In a specific embodiment, the said ester is 17-hydroxyprogesterone caproate.

The ester of 17-hydroxyprogesterone can be a substrate to the P-glycoproteins (P-gp) the efflux transporter systems. Hence, in one embodiment, the oral bioavailability can be enhanced by at least 10% by co-administering the ester of 17-hydroxyprogesterone of the current invention with an effective amount of P-gp and/or CYP3A4 inhibiting agents e.g., star fruit, grape fruit juice, bergamottin, cafestol (as in unfiltered coffee), ketoconazole, erythromycin, mibefradil, loperamide etc.

In a further aspect, the oral pharmaceutical compositions or the oral dosage forms of the ester of 17-hydroxyprogesterone according to the current invention can be used for providing luteal support for a subject in need thereof. In one embodiment, the oral composition or the oral dosage form can be formulated to enable modulation or titration of the dose and/or dosing regimen of the ester of 17-hydroxyprogesterone for providing effective luteal support to a subject in need thereof. In one particular embodiment, the dose of the ester of 17-hydroxyprogesterone in the form of oral compositions or dosage forms of the present invention may be modulated or titrated to provide effective luteal support as needed at the during early pregnancy. In another particular embodiment, the dose of the ester of 17-hydroxyprogesterone in the form of oral compositions or dosage forms of the present invention may be modulated or titrated to provide effective luteal support as needed based on the body mass index (BMI) of the subject. In another particular embodiment, the dose of the ester of 17-hydroxyprogesterone in the form of oral compositions or dosage forms of the present invention may be modulated or titrated to provide effective luteal support as needed based on the race or ethnicity of the subject.

An example of the dose modulation or titration can be based on the total dose per day, and can include administration of a higher initial loading dose or bolus dose, followed by a lower effective standard dose. Similarly, the dose modulation or titration can be based on the total dose per week and can include administration of a higher initial loading dose or bolus dose in the initial days of the week followed by a lower effective standard dose in the later days of the week. The dosing regimen can include ramping up of (i.e. progressive increments) the daily dose in accordance with the progression of pregnancy. In a specific embodiment the ester is 17-hydroxyprogesterone caproate (17-hydroxyprogesterone caproate).

In another embodiment, the daily oral dose administered with food of 17-hydroxyprogesterone caproate is from about 40 mg to about 5000 mg. In another embodiment, the daily oral dose is from about 40 mg to about 4000 mg. In another embodiment, the daily oral dose is from about 80 mg to about 4000 mg. In another embodiment, the daily oral dose is from about 150 mg to about 4000 mg. In another embodiment, the daily oral dose is from about 250 mg to about 4000 mg. In another embodiment, the daily oral dose of is from about 500 mg to about 4000 mg. In another embodiment, the daily oral dose is from about 750 mg to about 4000 mg. In another embodiment, the daily oral dose is from about 1000 mg to about 4000 mg. In another embodiment, the daily oral dose is from about 1200 mg to about 4000 mg. In another embodiment, the daily oral dose is from about 1500 mg to about 4000 mg. In another embodiment, the daily oral dose is from about 1500 mg to about 3000 mg. In another embodiment, the daily oral dose is from about 1000 mg to about 2000 mg. In another embodiment, the daily oral dose is from about 200 mg to about 2000 mg. In another embodiment, the daily oral dose is from about 400 mg to about 2000 mg. In another embodiment, the daily oral dose is from about 800 mg to about 2000 mg.

In one particular embodiment the oral dosage form of the current invention comprises a therapeutically effective amount of an ester of 17-hydroxyprogesterone, wherein, when measured using a USP Type-II dissolution apparatus in 900 mL of deionized water with 0.5% (w/v) of sodium lauryl sulfate at 50 RPM at 37° C., the oral dosage form releases at least 20 wt % of the dose of the ester of 17-hydroxyprogesterone after 60 minutes, In another particular embodiment, the dosage form releases at least about 40 wt % of the dose of the ester of 17-hydroxyprogesterone after 60 minutes. In another particular embodiment, the dosage form releases at least about 50 wt % of the dose of the ester of 17-hydroxyprogesterone after 60 minutes. In another particular embodiment, the dosage form releases at least about 70 wt % of the dose of the ester of 17-hydroxyprogesterone after 60 minutes. In a specific embodiment the ester is 17-hydroxyprogesterone caproate. In another embodiment, the dosage form is administered with food.

Following oral administration of the ester of 17-hydroxyprogesterone (e.g. 17-hydroxyprogesterone caproate) in the form of the composition or dosage form the present invention, its concentration in the serum, plasma or blood of the subject may be determined by analytical techniques based on radio-immunoassay (MA), high performance liquid chromatography—Mass Spectroscopy (HPLC-MS/MS) and the like. Accordingly, the plasma or blood levels for the ester may be different. It has to be understood that any relative comparisons of blood plasma levels of any compound should be made with the same assay methodology, or corrections must be made to adjust for discrepancy for assay specificity.

Accordingly, in one embodiment, the 17-hydroxyprogesterone caproate compositions or dosage forms of the present invention can provide a mean steady state 17-hydroxyprogesterone caproate mean $C_{max}$ from about 10 ng/mL to about 800 ng/mL, wherein the plasma 17-hydroxyprogesterone caproate is determined by HPLC-MS/MS method. In a particular embodiment, the compositions or dosage forms provides a mean steady state 17-hydroxyprogesterone caproate mean $C_{max}$ from about 10 ng/mL to about 400 ng/mL.

In further embodiment, the 17-hydroxyprogesterone caproate compositions or oral dosage forms of the present invention can provide a 17-hydroxyprogesterone caproate mean steady state $C_{min}$ of about 1 ng/mL or more. The plasma concentrations of the 17-hydroxyprogesterone caproate can be determined by HPLC-MS/MS method. In one embodiment, the compositions or oral dosage forms can provide a 17-hydroxyprogesterone caproate mean steady state $C_{min}$ greater than about 10 ng/mL. In another embodiment, the composition or oral dosage forms can provide a 17-hydroxyprogesterone caproate mean steady state $C_{min}$ greater than about 20 ng/mL, or greater than about 40 ng/ml, greater than about 60 ng/mL, or greater than about 80 ng/mL. In one specific embodiment, the composition or oral dosage form can provide a mean steady state $C_{min}$ of about 1 to about 60 ng/mL. In another specific embodiment, the composition or dosage form can provide a mean steady state $C_{min}$ of about 1 ng/mL to about 20 ng/mL.

Accordingly, the oral dosage form of 17-hydroxyprogesterone caproate of the present invention can be an immediate release dosage form. In a separate embodiment, the oral dosage form of the 17-hydroxyprogesterone caproate of the present invention can be a controlled release dosage form. In another specific embodiment, dosage form can include 17-hydroxyprogesterone caproate in the form of both immediate release and controlled release fractions, preferably extended or delayed release Consequently, the controlled release 17-hydroxyprogesterone caproate compositions or dosage forms of the present invention can provide a fluctuation in the 17-hydroxyprogesterone caproate levels less than about 795 ng/mL, wherein the fluctuation is determined by the difference of the mean steady state $C_{max}$ and the mean steady state $C_{min}$ of 17-hydroxyprogesterone caproate in plasma or serum or blood, upon oral administration.

In a another particular aspect, the oral pharmaceutical compositions and/or dosage forms of 17-hydroxyprogesterone caproate of the current invention can be used for the treatment of one or more of the conditions selected from the group consisting of habitual abortion, recurrent abortion, threatened abortion, post-partum after pains, endometrial cancer, management of primary and secondary amenorrhea, infertility due to corpus luteum insufficiency, deficiency of progestogen, cervical insufficiency, cervical incompetency, and abnormal uterine bleeding. In a further embodiment, the oral pharmaceutical compositions and/or dosage forms of 17-hydroxyprogesterone caproate of the current invention can be used in for testing endogenous estrogen production, and for the production of secretory endometrium and desquamation.

In another embodiment, the oral pharmaceutical compositions and/or dosage forms of 17-hydroxyprogesterone caproate of the current invention can be used along with omega-3 fatty acid supplementation to treat symptomatic preterm labor patients. In a particular embodiment, the current invention compositions and/or dosage forms may include at least one omega fatty acid. In another particular embodiment, the current invention compositions and/or dosage form may include omega-3, omega-6 or omega-9 fatty acid or mixtures thereof.

EXAMPLES

The following examples are provided to promote a more clear understanding of certain embodiments of the present invention, and are in no way meant as a limitation thereon. Unless otherwise specified or mentioned, all the compositions provided in the examples are with respect to % w/w of the final composition. Note that with the exception of the compositions listed in Examples 1, 7, 10, 17 and 36, the 17-hydroxyprogesterone caproate of all other example compositions can be in either treated (milled, micronized, or nanosized) or untreated form. The 17-hydroxyprogesterone Caproate in compositions 1, 7, 10, 17 and 36 are untreated for size reduction (i.e. unmilled, non-micronized, un-micronized or non-nanosized), and have an average particle size greater than 50 micrometers. The dosage forms of corresponding Examples were tested for release of the 17-hydroxyprogesterone caproate using a USP Type II apparatus, 50 rpm in 900 mL of "simulated intestinal fluid having 0.5% w/w sodium lauryl sulfate at 37° C. The percent of the 17-hydroxyprogesterone caproate released from each composition was analyzed using HPLC.

Examples 1-6-17-hydroxyprogesterone Caproate Compositions 17-hydroxyprogesterone caproate compositions as recited in Examples 1 through 6 are prepared by using the respective components shown in Table I. Example 1 is the untreated crystalline form of 17-hydroxyprogesterone caproate filled into hard gelatin capsule. Example 2 is micronized 17-hydroxyprogesterone caproate without a carrier filled into hard gelatin capsule. Examples 3-6, are prepared as follows: The required quantities of each of the components of the respective composition, except 17-hydroxyprogesterone caproate are taken in a clean stainless steel container and mixed at about 50° C. to 70° C. using a stirrer. A molten clear-to-hazy mixture is obtained. The required amount of the 17-hydroxyprogesterone caproate is added to the clear-to-hazy mixture and stirred to form a homogenous liquid mixture. A predetermined weight of the resulting liquid mixture is disposed into appropriate size capsules according to the 17-hydroxyprogesterone caproate dose required. The capsules are allowed to solidify at room temperature and then banded, and packaged into HDPE bottles and sealed with a lid.

The 17-hydroxyprogesterone caproate released from each of the compositions using the aforementioned dissolution testing parameters are shown in Table I. It should be noted that the Examples 1 & 2 (17-hydroxyprogesterone caproate without a carrier) and Examples 3 to 6 (17-hydroxyprogesterone caproate admixed with at least one carrier) can be used for comparison purposes to help illustrate the advantages of the compositions and dosage forms of the current invention.

TABLE I

| Ingredients | Example No. | | | | | |
| --- | --- | --- | --- | --- | --- | --- |
| | 1 | 2 | 3 | 4 | 5 | 6 |
| | Composition in % w/w. | | | | | |
| 17-hydroxyprogesterone caproate | 100 | 100* | 12 | 15 | 11 | 18 |
| Lipophilic additive: Ex: Castor Oil NF | — | — | 53 | — | 48 | — |
| Lipophilic additive: Ex: Lauroglycol FCC | — | — | 35 | — | 32 | — |
| Lipophilic additive: Glyceryl Monolinoleate, NF | — | — | — | 63 | — | 75 |
| Hydrophilic additive: Polyoxyl 40 Hydrogenated Castor Oil, NF | — | — | — | 16 | — | — |
| Hydrophilic additive: PEG 8000 USP | — | — | — | 6 | 9 | 7 |
| % release in 60 mins | <10 | >70 | >70 | >70 | >70 | >70 |

*micronized 17-hydroxyprogesterone caproate (approximate particle size distribution: d100% <25 μm; d50% <15 μm)

The aqueous dispersion of the mixture that includes a lipophilic additive and a hydrophilic surfactant, if present, of the Examples 3 to 6 of Table-I can be hazy to non-clear when viewed with a naked eye. Their absorbance at 400 nm can be greater than 0.1, or greater than 0.3, and/or the particle size of the dispersion can be greater than 100 nm. In some aspects, the average particle size of the dispersion may be greater than 250 nm. Each of the aqueous dispersions is prepared by mixing 1 part of the mixture of the additives of the corresponding example and 99 parts of an aqueous diluent. The compositions of Example 3-6 may be prepared by mixing the additives the 17 hydroxyprogesterone caproate to get a homogenous solution or suspension. If required, the mixture may be heated (for example, to about 40° C. to about 80° C.) to get a solution or to achieve a homogenous suspension. The mixture can be disposed into a capsule. The dosage form of Example 1 and 2 has 17-hydroxyprogesterone caproate in the solid unmicronized and micronized particulate form respectively. The 17-hydroxyprogesterone caproate can be fully solubilized (as in case of Example 3) or partially solubilized (as in case of Examples 5 and 6). The formulations of Table I, if liquid, can be also formulated to be a solid dosage form by filling either as is, or admixed with a solidification aid, into a capsule. Alternatively, they can be formulated into tablets by using appropriate tableting aids.

Examples 7-10-17-hydroxyprogesterone Caproate Compositions 17-hydroxyprogesterone caproate compositions of Examples 7 through 10 can be prepared by using the ingredients shown in Table II and attain the release performance indicated.

TABLE II

| | Example No. | | | |
|---|---|---|---|---|
| | 7 | 8 | 9 | 10 |
| Ingredients | Composition in % w/w. | | | |
| 17-hydroxyprogesterone caproate (particle size > 50 μm) | 90-99 | — | — | 90-99 |
| 17-hydroxyprogesterone caproate micronized* | — | 70-80 | — | — |
| 17-hydroxyprogesterone caproate (milled) | — | — | 70-80 | — |
| Lactose | 1-10 | 1-20 | 1-20 | 30 |
| Povidone K30 | 3-6 | 3-6 | 3-6 | 3-6 |
| Organic granulating solvent (example, alcohol)** | — | 0 or q.s*** | 0 or q.s*** | q.s*** |
| % release in 60 mins | <15 | >50 | >50 | >30 |

*may be substituted with nanomilled or nanosized 17-hydroxyprogesterone caproate.
**removed substantially during drying process
***Quantity sufficient for wet granulation process or for in situ formation/precipitation of fast releasing solid 17-hydroxyprogesterone caproate It should be noted that the compositions of Examples 7 to 10 can be formulated to provide granules for compression into a tablet or filling in a capsule, sachet etc., with the inclusion of appropriate pharmaceutical aids such as diluents, binder, disintegrant, lubricants, flavor, etc.

Unlike Example 1 and 7, the 17-hydroxyprogesterone caproate release profile of Examples 8, 9 and 10, shown in Table II, illustrate the advantages of the smaller particle size of 17-hydroxyprogesterone caproate. These Examples further illustrate the advantages of various manufacturing processes, such as granulation, which yield solid compositions with appropriate 17-hydroxygprogesterone caproate release profiles. In some embodiments, the caproate ester in the compositions of examples in Table II can be substituted with other esters of 17-hydroxyprogesterone, such as acetate or undecanoate.

Example 11-17-hydroxyprogesterone Caproate Coated Tablets 17-hydroxyprogesterone caproate tablets of Example 7 through 10 can be further coated with a coating solution having typical composition set forth in Table III, using conventional tablet coating procedures known in the art to a weight gain of about 3 to 6%.

TABLE III

| Ingredients | Composition in % w/w |
|---|---|
| Polymer (for e.g. Hypromellose, Methocel E 5) | 8.0 |
| Plasticizer (e.g. Polyethylene glycol, NF 8000) | 0.6 |
| Coating Solvent (e.g. Ethanol) | 54.8 |
| Coating Solvent Water | 36.6 |

The coating polymer can be selected based on the need for a specific functionality to be imparted to the dosage form. For example film coating, taste masking, enteric coating protective coating, sustained release coating and so on can all be used. Unlimited examples of the polymers for use in such coatings include hypromellose, polyethylene glycol, povidone, sugars, ethyl celluloses, methacrylates, cellulose phthalates etc. Many conventional coating aids such as talc, starch, plasticizers, opacifiers, colors, flavors etc. can also be used along with coating polymers or sugars. The coating solvents can be suitably varied based on the coating polymer or sugar being applied.

Examples 12-17-17-hydroxyprogesterone Caproate Compositions

Table IV shows the 17-hydroxyprogesterone caproate compositions of Examples 12-17 that can be prepared by using the components set forth therein and the method similar to that described for Examples 3-6. The release of 17-hydroxyprogesterone caproate from the dosage form is also shown in Table IV.

TABLE IV

| | Example No. | | | | | |
|---|---|---|---|---|---|---|
| | 12 | 13 | 14 | 15 | 16 | 17 |
| Ingredients | Composition % w/w | | | | | |
| 17-hydroxyprogesterone caproate | 15 | 15 | 14 | 15 | 22 | 25 |
| Lipophilic Additive . . . (example Glyceryl Caprylate/Caprate (Capmul ®MCM) | — | 85 | — | — | — | — |
| Lipophilic Additive (e.g . . . Capric Acid) | 85 | — | — | — | — | — |
| Lipophilic Additive (e.g Glyceryl Monolinoleate) | — | — | 73 | 65 | 3 | 5 |
| Hydrophilic Additive (e.g. Polyoxyl 40 Hydrogenated Castor Oil) | — | — | 13 | 15 | — | — |
| Hydrophilic Additive (e.g. Polyoxyl 35 Castor Oil) | — | — | — | — | — | 22 |
| Lipophilic Additive (e.g Glyceryl Palmitostearate; Glyceryl distearate, Precirol ® ATO 5) | — | — | — | 5 | — | — |
| Hydrophilic Additive (e.g. Tocopherol Polyethylene Glycol Succinate) | — | — | — | — | 22 | — |
| Lipophilic Additive (e.g Vitamin E; d,l-α-tocopherol) | — | — | — | — | 35 | 48 |
| Hydrophilic Additive (e.g. Hypromellose (4,000 cPs) | — | — | — | — | 18 | — |
| % release in 60 mins | >40 | >40 | >40 | >40 | >30 | >40 |

The aqueous dispersion of the mixture of lipophilic additive and the hydrophilic surfactant, if present, in the examples shown in Table-IV can be hazy to non-clear when viewed with the naked eye. Their absorbance at 400 nm can be greater than 0.1, or greater than 0.3, and/or the particle size of the dispersion can be greater than 100 nm. In some aspects, the mean particle size of the dispersion may be greater than 250 nm. Each of the aqueous dispersions is prepared by mixing 1 part of the mixture of the additives of the corresponding example and 99 parts of an aqueous diluent.

The compositions of Table IV, if liquid, can be formulated to be solid dosage forms by filling into a capsule either as is, or admixed with a solidification aid such as polyethylene glycol, glyceryl distearate, wax and the like. It should be noted that these compositions can also be formulated to obtain granules for compression into a tablet or filling into a capsule, sachet etc., with the inclusion of appropriate pharmaceutical aids such as diluents, binders, disintegrants, lubricants, flavors, etc.

The 17-hydroxyprogesterone caproate in the compositions of examples in Table IV can in some embodiments be substituted with other esters of 17-hydroxyprogesterone, such as 17-hydroxyprogesterone acetate or 17-hydroxyprogesterone undecanoate.

Examples 18-23-17-hydroxyprogesterone Caproate Compositions

Table V shows various 17-hydroxyprogesterone caproate compositions as recited in Examples 18-23 that can be prepared using the components set forth therein.

TABLE V

| INGREDIENT | Example No. | | | | | |
|---|---|---|---|---|---|---|
| | 18 | 19 | 20 | 21 | 22 | 23 |
| | Composition % w/w | | | | | |
| 17-hydroxyprogesterone caproate | 9 | 7 | 6 | 8 | 8 | 6 |
| Hydrophilic Surfactant (e.g. Tween 80) | 1 | 1 | 1 | 4 | 1 | 1 |
| Hydrophilic Surfactant (e.g. Sodium Lauryl Sulfate) | 4 | 4 | 3 | 1 | 4 | 3 |
| Hydrophilic Polymer (e.g. HPMC) | — | 15 | 26 | 5 | — | 25 |
| Enteric Polymer (e.g. Eudragit) | — | — | — | — | — | 4 |
| Hydrophobic Polymer (e.g. Ethyl Cellulose) | — | — | — | — | 5 | — |
| Diluents/Processing Aids | 86 | 73 | 64 | 82 | 82 | 61 |
| Total | 100 | 100 | 100 | 100 | 100 | 100 |

Table VI shows various specific embodiments of different dosage forms (DF-1 to DF-9) containing 17-hydroxyprogesterone caproate that can be achieved by various combinations of the compositions shown in Table V.

TABLE VI

| Composition Example No. | Dosage Form | | | | | | | | |
|---|---|---|---|---|---|---|---|---|---|
| | DF-1 | DF-2 | DF-3 | DF-4 | DF-5 | DF-6 | DF-7 | DF-8 | DF-9 |
| | Composition % w/w | | | | | | | | |
| 18 | 100 | 50 | 50 | 50 | 30 | — | — | 30 | 50 |
| 19 | — | 50 | — | — | — | — | — | — | — |
| 20 | — | — | 50 | — | — | 100 | — | 30 | — |
| 21 | — | — | — | 50 | — | — | — | 40 | 50 |
| 22 | — | — | — | — | — | — | 100 | — | — |
| 23 | — | — | — | — | 70 | — | — | — | — |
| Total | 100 | 100 | 100 | 100 | 100 | 100 | 100 | 100 | 100 |

Additional tableting methods known in the art can be used can be applied to the above exemplified compositions.
Excipients shown are exemplary of classes of excipients that can be used
The form of the drug can be interchanged with other forms such as micronized, sieved, milled, amorphous, nano, etc.
The above dosage forms DF-1 to DF-9 can be single or multiple particulate units in a capsule or as single or multiple particulate units compressed into a single tablet or multi-layer tablets.

Examples 24-28-17-hydroxyprogesterone Caproate Compositions

Table VII shows 17-hydroxyprogesterone caproate compositions as recited in Examples 24-28 that can be prepared using the components set forth therein, and their release performance.

TABLE VII

| INGREDIENT | Example No. | | | | |
|---|---|---|---|---|---|
| | 24 | 25 | 26 | 27 | 28 |
| | Composition (mg per dosage form) | | | | |
| 17-hydroxyprogesterone | 50 | 50 | 50 | 50 | 50 |
| Hydrophilic Surfactant (e.g. Tween 80) | 2.5 | 2.5 | 2.5 | 2.5 | 2.5 |
| Hydrophilic Surfactant (e.g. Sodium Lauryl Sulfate) | 12.5 | 12.5 | 12.5 | 12.5 | 12.5 |
| Hydrophilic Polymer (e.g. HPMC) | 125 | 65 | 90 | — | 3 |
| Enteric Polymer (e.g. Eudragit) | — | — | — | — | 5 |
| Coating Processing Aids (e.g. Plasticizer, Anti-sticking agent) | — | — | — | — | 2 |
| Diluents/Processing Aids (e.g. binder, disintegrant, diluent, glidant, lubricant) | 25 | 25 | 35 | 35 | 35 |
| Total | 215 | 155 | 190 | 100 | 110 |
| % Release in 60 minutes | >25 | >40 | >40 | 100 | >30 |

Additional tableting methods known in the art can be used can be applied to the above exemplified compositions.
Excipients shown are exemplary of classes of excipients that can be used, processing aids like binders, disintegrants, diluents, glidants, lubricants and coating aids commonly known in the art can be used.
The form of the drug can be interchanged with other forms such as micronized, sieved, milled, amorphous, nano, etc.
The above dosage forms can be single or multiple particulate units in a capsule or as single or multiple particulate units compressed as a monolithic/matrix tablet or multi-layer tablets For Example 28 the dosage form is first exposed to about 250 mL simulated gastric fluid (SGF) without enzyme for the first 30 minutes, followed by exposure to 900 mL of 0.5 wt % SLS in water at having pH about 6.8.

Examples 29-35-17-hydroxyprogesterone Caproate Compositions

Table VIII shows 17-hydroxyprogesterone caproate compositions and release data for Examples 29-35 that can be prepared by using components set forth therein and the method similar to that described for Examples 12-17.

TABLE VIII

| Ingredients | Example No. | | | | | | |
|---|---|---|---|---|---|---|---|
| | 29 | 30 | 31 | 32 | 33 | 34 | 35 |
| | Composition % w/w | | | | | | |
| 17-hydroxyprogesterone caproate | 25 | 20 | 7 | 7 | 8 | 16 | 25 |
| Lipophilic Additive (e.g. Benzyl benzoate) | 48 | 45 | — | — | — | 29 | 53 |
| Hydrophilic Additive (e.g. Benzyl alcohol) | 2 | 2 | — | — | — | — | 2 |
| Lipophilic Additive (e.g. Castor Oil) | 25 | 23 | — | — | — | — | — |
| Lipophilic Additive (e.g. Corn glycerides) | — | — | — | — | 67 | — | — |
| Lipophilic Additive (e.g. Glyceryl Caprylate/Caprate; Capmul ®MCM) | — | — | 51 | 48 | — | 17 | — |
| Lipophilic Additive (e.g. Capric Acid) | — | — | — | — | — | — | — |
| Hydrophilic Additive (e.g Polyoxyl 40 Hydrogenated Castor Oil) | — | 10 | 42 | 40 | 25 | 38 | 10 |
| Hydrophilic Additive (e.g Polyethylene glycol 8000) | — | — | — | 5 | — | — | 10 |
| % release in 60 mins | >25 | >25 | >90* | >80 | >60 | >60 | >25 |

*% released in 30 minutes

The above compositions can be formulated to exhibit immediate or controlled release profiles. The aqueous dispersion of the mixture of the lipophilic additive and the hydrophilic surfactant, if present, in the examples of Table-VIII can be hazy to non-clear when viewed with the naked eye. Their absorbance at 400 nm are greater than 0.1, in some cases greater than 0.3, and/or the average particle size of the dispersion may be greater than 100 nm in some aspects. In other aspects, the average particle size of the dispersion can be greater than 250 nm. Each of the aqueous dispersions is prepared by mixing 1 part of the mixture of the additives and surfactants of the corresponding example and 99 parts of an aqueous diluent.

As can be seen from the above Examples 29, 30 and 35 by using benzyl benzoate and/or benzyl alcohol, a higher drug loading (e.g. ≥20% w/w 17-hydroxyprogesterone caproate) with desired release characteristics can be achieved. The 17-hydroxyprogesterone caproate can remain fully solubilized (Examples 29, 30, 31, and 33) or can be partially solubilized (Examples 32, 34 and 35) in the compositions. Further, when viewed with the naked eye the aqueous dispersion of the mixtures having a lipophilic additive and the hydrophilic surfactant, if present, as recited in Examples 29-31 and 33-35 can be hazy to non-clear. In some cases, their absorbance at 400 nm is greater than 0.1, or even greater than 0.3. Further the average particle size of the dispersion can be greater than 100 nm, or even greater than 250 nm. Each of the aqueous dispersions is prepared by mixing 1 part of the mixture of the additives and surfactants of the corresponding example and 99 parts of an aqueous diluent.

The 17-hydroxyprogesterone caproate in the compositions of examples in Table VIII can in some aspects substituted with other esters of 17-hydroxyprogesterone, such as 17-hydroxyprogesterone acetate or 17-hydroxyprogesterone undecanoate.

The compositions of example 3, 31, 32, 33, and 34 can in some aspects, also be administered as oral liquid. These compositions can also be administered orally after appropriate admixture/dilution with diluent such as water, milk, fruit juices, beverages and the like just before administration.

In certain embodiments, the contents of the above compositions can be adsorbed on some diluents and additional excipients and can be compress into tablet.

Example 36-17-hydroxyprogesterone Caproate Tablets 17-hydroxyprogesterone caproate containing granules for tableting having the components set forth in Table IX can be prepared by wet granulation methods. Accordingly, 17-hydroxyprogesterone caproate, microcrystalline cellulose and croscarmellose sodium are passed through an ASTM mesh #40 mesh sieve and mixed in a low shear granulator to form a uniform blend. A binder solution of Starch 1500 in deionized water can be used to granulate the dry powder blend to a typical granulation end-point. The wet granulate dried using a tray dryer or fluid air dryer can be sized/screened, lubricated with Aerosil 200 and magnesium stearate, and compressed into tablets.

TABLE IX

| Ingredients | Composition in % w/w |
|---|---|
| 17-hydroxyprogesterone caproate (untreated) | 28 |
| Microcrystalline Cellulose (Avicel PH 102) | 52.5 |
| Croscarmellose sodium | 10 |
| Pregelatinized starch (Starch1500) | 8 |
| Colloidal silicon dioxide (Aerosil 200) | 0.5 |
| Magnesium stearate | 1 |

The tablets of Example 36 exhibit less than 20% 17-hydroxyprogesterone caproate released in the first 60 minutes when tested using a USP Type II apparatus, 50 rpm in 900 mL of simulated intestinal fluid having 0.5% w/w sodium lauryl sulfate at 37° C. Whereas, when the micronized 17-hydroxyprogesterone caproate (with particle size d100% being about 50 µm or less) with or without surfactant is used in the above formula, at least 40% release of 17-hydroxyprogesterone caproate may be observed after the 60 minute time-point.

Examples 37-42-17-hydroxyprogesterone Caproate Compositions

Examples 37-39 of Table X have hydrophilic additives as carriers. The Examples 37, 38 and 39 therein are prepared by wet granulation process with organic solvent such as ethanol or ethanol-water as the granulating liquid. Partial or full amounts of some of hydrophilic additives therein (e.g. povidones, pluronics, surfactants etc.) can be dissolved in the granulating liquid. Optionally the ester of 17-hydroxyprogesterone (e.g. 17-hydroxyprogesterone caproate) can be solubilized or suspended in the granulating liquid. This granulating liquid can then be poured over the adsorbing hydrophilic carriers (e.g. celluloses, Lactose etc.) with low shear mixing. The granules can be dried under a gentle current of air at room temperature. The dried granules are passed through ASTM #40 mesh and filled into appropriate size capsules or compressed into tablets according to the required 17-hydroxyprogesterone caproate strength per unit dosage form.

17-hydroxyprogesterone caproate compositions of Examples 40-42 can be prepared by using the components set forth in Table X and according to the following method: The required quantities of the respective inactive component and the 17-hydroxyprogesterone caproate, are taken in a clean stainless steel container and mixed gently at about 50° C. to 70° C. using a stirrer, to get a homogenous mixture. A predetermined weight of the resulting mixture is disposed into hard gelatin capsule and allowed to solidify at room temperature.

The dosage forms of each Example 37-42 are tested for release of the 17-hydroxyprogesterone caproate using a USP Type II apparatus, at 50 rpm in 900 mL of simulated intestinal fluid having 0.5% w/w sodium lauryl sulfate at 37° C. The percent of the 17-hydroxyprogesterone caproate released from each composition is analyzed using HPLC. The results of the release testing are also shown in Table X.

It should be noted that the compositions of Examples 37-42 can be formulated to achieve tablet dosage forms with the inclusion of appropriate conventional tableting aids such as diluents, binders, disintegrants, lubricants, etc. as needed.

The in vitro 17-hydroxyprogesterone caproate release performance of Examples 37 to 42 can be seen to be superior over the release performance of the Example 36. It should be noted that in the above-recited compositions, appropriate amounts of typical pharmaceutical aids such as glidants, lubricants, anti-adherents, disintegrants and the like, can be incorporated as needed. Further, suitable amounts of hydrophilic release modifying agents (e.g. hypromellose, Eudragits etc.) may also be incorporated as needed in the compositions of Examples 37 to 42. Also, in some particular cases, when the dosage form of the Examples 37 to 42 is a tablet, appropriate functional coatings may be applied as required. It should also be noted that in some aspects the example compositions of Table X can be substituted with other esters of 17-hydroxyprogesterone (e.g. 17-hydroxyprogesterone acetate, 17-hydroxyprogesterone undecanoate, etc.)

Examples 43 and 44-17-hydroxyprogesterone Caproate Compositions 17-hydroxyprogesterone caproate compositions as recited in Examples 43 and 44 were prepared by using the components set forth in Table XI. Each of the compositions was prepared by incorporating 17-hydroxyprogesterone caproate in the molten mixture of the corresponding inactive components taken in a stainless steel container at about 35° C. to 70° C. with gentle stirring to get a free-flowing liquid mixture. A predetermined weight of the resulting liquid mixture is disposed into hard or soft gelatin capsule shells and allowed to solidify at room temperature. It should be noted that the liquid mixture can also be allowed to solidify to room temperature to get solid aggregates which may be sized through an ASTM mesh #30 to get granular particulates, which can be further filled in hard gelatin capsules or compressed into tablets.

Each of the compositions is tested for release of the 17-hydroxyprogesterone caproate using a USP Type II apparatus, at 50 rpm in 900 mL of simulated intestinal fluid having 0.5% w/w sodium lauryl sulfate at 37° C. The percent of the 17-hydroxyprogesterone caproate released from each composition is analyzed using HPLC. The results of the release testing are also shown in Table XI.

TABLE XI

| Ingredients | Example No. 43 | Example No. 44 |
| --- | --- | --- |
|  | Composition in % w/w | |
| 17-hydroxyprogesterone caproate | 20 | 80 |
| Lipophilic additive: (e.g. Glycerol esters of $C_{12}$-$C_{18}$ fatty acids) | 80 | 20 |
| % release in 60 mins | >30% | >30% |

Example 45-17-hydroxyprogesterone Caproate Spray Dried Multiparticulates 17-hydroxyprogesterone caproate multiparticulates can be prepared as follows: 15 g of a milled or micronized 17-hydroxyprogesterone caproate and lactose, mixture (95:5 w/w), are passed through ASTM mesh #60 sieve and added under mixing to about 250 mL of a solution of 8% w/v povidone K17 in water. The resulting suspension can be spray dried using a conventional spray drying equipment with settings, for example, at a heat inlet temperature of about 60-75° C. and an outlet temperature of about 30-38°

TABLE X

| Ingredients | 37 | 38 | 39 | 40 | 41 | 42 |
| --- | --- | --- | --- | --- | --- | --- |
|  | Composition in % w/w | | | | | |
| 17-hydroxyprogesterone caproate | 45 | 40 | 40 | 75 | 34 | 60 |
| PEG 8000 USP | — | — | — | 10 | 29 | 40 |
| Sodium Lauryl sulfate | 10 | 9 | 9 | 10 | — | — |
| Microcrystalline Cellulose*, | 45 | 40 | 37 | — | — | — |
| Pluronic F 68 | 0 | 11 | 11 | — | — | — |
| Polyvinylpyrrolidone (Povidone K 30) | 0 | 0 | 3 | 5 | 37 | — |
| % release in 60 mins | >40 | >40 | >40 | >40 | >40 | >30 |

*Magnesium alumnometasilicate (Neuslin ®), lactose and other similar substances can be used/calcium silicate C., aspirator set at 90-100%, the pump set at about 8-12 mL/min, and the flow rate set at about 500-600 L/hr. The final solid multiparticulate 17-hydroxyprogesterone caproate composition can have a compositional makeup of about 53 wt % 17-hydroxyprogesterone caproate, about 2.8 wt % lactose and about 44.2 wt % povidone K17.

Example 46-50-17-hydroxyprogesterone Caproate Compositions

A mixture of 17-hydroxyprogesterone caproate and the corresponding components can be melted together to get thermosetting fill to be disposed into capsule. Alternatively, the mixture can be fed into a melt-extruder apparatus for example, a single-screw extruder (Killion, Model KLB 100) equipped with about 1 inch diameter screw and about 6 inch flex lip die, and the die opening adjusted to about 0.005 inches and the screw speed is set at about 50 rpm. The residence time of the materials within the extruder can be set for about 2 to 8 minutes. The extruded strands can be cooled to room temperature by passing over a chilled roll. The strands can then be sized through an ASTM mesh #40 and the powder disposed into capsules. The exemplary compositions for melt-extrusion are indicated in Table XII. These dosage forms can release 40% or more 17-hydroxyprogesterone caproate in about first 60 minutes. It should be noted that the 17-hydroxyprogesterone caproate compositions of Table XII can be further formulated to include one or more other substances such as lactose, starches, hydroxypropyl methyl cellulose, methacrylate, etc., at varying concentrations from about 12% to about 88% by weight of the total composition either prior to melt-extrusion or after sizing the melt-extruded composition, in order to prepare solid multiparticulates for tablets.

TABLE XII

| Ingredients | Example No. | | | | |
|---|---|---|---|---|---|
| | 46 | 47 | 48 | 49 | 50 |
| | Composition in % w/w | | | | |
| 17-hydroxyprogesterone caproate | 70 | 40 | 50 | 80 | 60 |
| Polyethylene glycol 8000 USP | 10 | — | 20 | 15 | 20 |
| (Glyceryl distearate GDS, Precirol ATO 5) | 10 | 40 | 20 | — | — |
| Stearic acid | 10 | 20 | 10 | — | — |
| Cholesterol | — | — | — | 5 | 20 |

Example 51-17-hydroxyprogesterone Caproate Compositions Produced by Co-Milling

A 17-hydroxyprogesterone caproate containing composition can be prepared by co-milling (or co-grinding) 80 g 17-hydroxyprogesterone caproate along with 15 g PVP K 17 and 5 g of sodium lauryl sulfate for a period from about 12 hours to about 24 hours using a ceramic ball-mill maintained at about 20±5° C. The co-milled composition can provide a superior in vitro drug release profile which could be at least 20% more when compared to the in vitro release profile of Example 1 when tested using a USP Type II apparatus, 50 rpm in 900 mL of simulated intestinal fluid having 0.5% w/w sodium lauryl sulfate at 37° C.

Example 52-17-hydroxyprogesterone Caproate Loaded Pellets 17-hydroxyprogesterone caproate coated pellets are prepared using the ingredients set forth in Table XIII A spraying solution of the coating materials can be prepared by dissolving 25 g of 17-hydroxyprogesterone caproate, 6 g of Pluronic F 68 and 5 g of PVP K 30 in about 250 mL of dehydrated alcohol. The spray solution can be intermittently sprayed on to a rolling bed of 64 g commercially available microcrystalline cellulose spheres (for example, having a mean particle size in the range of about 250 µm to about 600 µm) taken in a conventional coating pan. After all the spray solution is loaded on the spheres, it can be dried under a gentle current of air for at least 1 hour to remove the solvent. Thus, by adjusting the pan speed, spray rate and the inlet air flow and temperature, the 17-hydroxyprogesterone caproate loaded pellets or beads can be obtained which can be disposed into a capsule. Auxiliary pharmaceutical process aids such as talc, starch etc., may be dusted during the spraying process to avoid agglomeration of the pellets.

It should be noted that appropriate similar or equivalent equipment known in the art may be used for the purpose. Also, by varying the quantity of spray solution sprayed on the spheres or by varying the concentration of 17-hydroxyprogesterone caproate in the spray solution, pellets of different drug loading can be achieved.

TABLE XIII

| Ingredients | Composition in % w/w |
|---|---|
| 17-hydroxyprogesterone caproate | 25 |
| Pluronic F 68 | 6 |
| Polyvinylpyrrolidone K 30 | 5 |
| Dehydrated Alcohol | 250 mL |
| Microcrystalline cellulose spheres (Celsphere ®) | 64 |

Example 53-17-hydroxyprogesterone Caproate Suspension Compositions

A homogenous suspension of 17-hydroxyprogesterone caproate prepared in a liquid vehicle having at least one non-solvent can be made by conventional processes known in the art. The suspension can be dosed as a conventional oral liquid or a known volume of the suspension may be encapsulated. Pharmaceutical aids such suspending agents, thickening agents or viscosity modifiers, wetting agents, etc., known in the art can be used to achieve homogenous suspension of the drug in the liquid vehicle.

Example 54-17-hydroxyprogesterone Caproate Composition In Vivo Evaluation

A preliminary pharmacokinetic evaluation upon oral administration of 17-hydroxyprogesterone caproate of the current invention was carried out in male dogs. A single oral dose of 30 mg/kg and 5 mg/kg of 17-hydroxyprogesterone caproate formulated in a accordance with exemplary formulations of the present invention were used for relative bioavailability study in a fed state, compared with an intramuscular dose of 6.4 mg/kg (composition similar to commercially available Intramuscular Injection, Makena®) as positive control.

The post-dose blood levels of 17-hydroxyprogesterone caproate were monitored for 24 hours after oral dosing and for 192 hours after intramuscular injection dosing. About 2 mL of blood was drawn from the jugular, cephalic, or saphenous veins immediately before the dose was administered and at pre-determined intervals post-dose. At each time point, the blood sample was collected in a vacutainer tubes and centrifuged at about 3200 rpm for approximately 10 minutes at about 5° C. The serum obtained was analyzed by HPLC-MS/MS for 17-hydroxyprogesterone caproate. The results of the 17-hydroxyprogesterone caproate concentration in the samples are shown in Table-XIV below:

TABLE XIV

| | Exemplary Oral Dosage formulations of the present invention | | IM Injection |
|---|---|---|---|
| Dose Administered | 30 mg/kg | 5 mg/kg | 6.4 mg/kg |
| Mean $C_{last}$ (ng/mL) | 4.51 | 0.28 | 2.54 |
| $C_{avg}$ (ng/mL) | 74 | 2.5 | 8 |
| Mean $AUC_{0\text{-}last}$ (ng * h/mL) | 1767 | 60 | 1546 |
| AUC (ng * h mL$^{-1}$)$_{0\text{-}24h}$/Dose (mg) Ratio | 5.8 | 1.0 | — |

Contrary to reports in the literature we surprisingly found that oral compositions of the present invention provided significant blood levels ($C_{avg}$) of 17-hydroxyprogesterone caproate upon oral administration.

Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that variations including, but not limited to, variations in size, materials, shape, form, function and manner of operation, assembly and use may be made without departing from the principles and concepts set forth herein.

What is claimed is:

1. A method of treating a pregnant female at risk of having a preterm birth, said method comprising administering to a pregnant female having one or more serum biomarkers that indicate said pregnant female is at risk of preterm birth a pharmaceutical composition comprising a therapeutically effective amount of 17-hydroxyprogesterone caproate and a pharmaceutically acceptable carrier comprising a lipophilic additive selected from benzyl benzoate, castor oil and mixtures thereof, said lipophilic additive comprising at least 50 weight/weight percent (w/w %) of the carrier and said pharmaceutical composition having 50 w/w % or less castor oil and 50 w/w % or less benzyl benzoate wherein said pharmaceutical composition is prepared by combining castor oil, benzyl benzoate and 17-hydroxyprogesterone caproate with the proviso that benzyl alcohol is not combined with the pharmaceutical composition.

2. A method of treating a pregnant female at risk of having a preterm birth, said method comprising administration to a pregnant female having one or more serum biomarkers that indicate said pregnant female is at risk of preterm birth a pharmaceutical composition having a therapeutically effective amount of 17-hydroxyprogesterone caproate and a pharmaceutically acceptable carrier comprising a lipophilic additive selected from benzyl benzoate, castor oil and mixtures thereof, said lipophilic additive comprising at least 50 weight/weight percent (w/w %) of the carrier and said pharmaceutical composition having 50 w/w % or less castor oil and 50 w/w % or less benzyl benzoate wherein said pharmaceutical composition when measured using a USP Type-II dissolution apparatus in 900 mL of simulated intestinal fluid having 0.5 w/w % sodium lauryl sulfate at 50 RPM at 37° C., releases at least 20% of the 17-hydroxyprogesterone caproate at 60 minutes with the proviso that the composition does not include benzyl alcohol.

3. The method of claim 2, wherein said pharmaceutical composition is in a capsule.

4. The method of claim 2, wherein said pharmaceutical composition is formulated as a tablet.

5. The method of claim 3, wherein said capsule includes from about 30 mg to about 300 mg of 17-hydroxyprogesterone caproate.

6. The method of claim 4, wherein said tablet includes from about 20 mg to about 800 mg of 17-hydroxyprogesterone caproate.

7. The method of claim 2, wherein said pharmaceutical composition is a controlled release dosage form.

8. The method of claim 2, wherein the pharmaceutical composition has from about 28 to about 48 w/w % benzyl benzoate.

9. The method of claim 2, wherein the pharmaceutical composition has from about 23 to about 25 w/w % castor oil.

10. The method of claim 2, wherein the pharmaceutical composition has about 5 to about 30 w/w 17-hydroxyprogesterone caproate.

11. The method of claim 2, wherein the pharmaceutical composition has about 25% w/w % 17-hydroxyprogesterone caproate.

12. The method of claim 2, wherein the pharmaceutical composition has the 17-hydroxyprogesterone caproate in a fully solubilized form.

* * * * *